(12) United States Patent
Masood et al.

(10) Patent No.: US 9,964,499 B2
(45) Date of Patent: May 8, 2018

(54) METHOD OF, AND APPARATUS FOR, MATERIAL CLASSIFICATION IN MULTI-ENERGY IMAGE DATA

(71) Applicant: Toshiba Medical Systems Corporation, Otawara-shi (JP)

(72) Inventors: Saad Masood, Edinburgh (GB); Costas Plakas, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days. days.

(21) Appl. No.: 14/532,143

(22) Filed: Nov. 4, 2014

(65) Prior Publication Data

US 2016/0123904 A1    May 5, 2016

(51) Int. Cl.
| G06K 9/00 | (2006.01) |
| G01N 23/04 | (2018.01) |
| G06K 9/62 | (2006.01) |
| G06T 11/00 | (2006.01) |

(52) U.S. Cl.
CPC ....... G01N 23/046 (2013.01); G06K 9/00536 (2013.01); G06K 9/6218 (2013.01); G06K 9/6277 (2013.01); G06T 11/008 (2013.01); G06T 2211/408 (2013.01)

(58) Field of Classification Search
CPC .............. G06T 2211/408; G06T 2207/10036
See application file for complete search history.

(56) References Cited

U.S. PATENT DOCUMENTS

| 6,058,205 A * | 5/2000 | Bahl .................... G06K 9/6282 382/159 |
| 6,597,759 B2 * | 7/2003 | Mazess .................. G01N 23/06 378/53 |
| 6,898,263 B2 * | 5/2005 | Avinash ................. A61B 6/032 378/4 |
| 7,050,533 B2 * | 5/2006 | Heismann .............. A61B 6/032 378/18 |
| 7,920,735 B2 | 4/2011 | Krauss et al. |
| 7,983,382 B2 * | 7/2011 | Thomsen ............... A61B 6/032 378/4 |
| 8,155,412 B2 * | 4/2012 | Kitamura ................. G06T 5/50 382/128 |

(Continued)

FOREIGN PATENT DOCUMENTS

| JP | 2007-268273 | 10/2007 |
| JP | 2010-253138 | 11/2010 |

(Continued)

OTHER PUBLICATIONS

Kwon ("Threshold selection based on cluster analysis", 2004).*

(Continued)

*Primary Examiner* — Avinash Yentrapati
(74) *Attorney, Agent, or Firm* — Oblon, McClelland, Maier & Neustadt, L.L.P.

(57) ABSTRACT

An apparatus for processing multi-energy image data to separate at least two types of material comprises a classification unit, wherein the classification unit is configured to obtain a classification of pixels or voxels belonging to the types of material based on a threshold which is adaptively changed in dependence on multi-energy intensity information associated with the pixels or voxels.

21 Claims, 27 Drawing Sheets

(56) References Cited

U.S. PATENT DOCUMENTS

| | | | | |
|---|---|---|---|---|
| 8,294,717 B2* | 10/2012 | Zamyatin | ............... | G06K 9/342 345/440 |
| 8,345,934 B2* | 1/2013 | Obrador | ............ | G06K 9/00677 382/100 |
| 8,731,334 B2* | 5/2014 | Lefebvre | ............ | G06K 9/00986 382/131 |
| 8,768,050 B2* | 7/2014 | Kannan | ................ | G06K 9/6293 382/112 |
| 9,204,847 B2* | 12/2015 | Flohr | .................... | A61B 6/4014 |
| 9,211,066 B2* | 12/2015 | Johnson | ................ | A61B 5/0033 |
| 9,211,104 B2* | 12/2015 | Krauβ | ..................... | A61B 6/482 |
| 2003/0215120 A1* | 11/2003 | Uppaluri | ................ | A61B 6/482 382/128 |
| 2004/0022438 A1* | 2/2004 | Hibbard | ................ | G06T 7/0012 382/199 |
| 2004/0101086 A1* | 5/2004 | Sabol | .................... | A61B 5/4872 378/4 |
| 2005/0010106 A1* | 1/2005 | Lang | ....................... | A61B 6/469 600/425 |
| 2006/0093209 A1* | 5/2006 | Guetter | ................ | G06K 9/6206 382/159 |
| 2007/0047794 A1* | 3/2007 | Lang | ..................... | G06T 7/0012 382/132 |
| 2007/0092056 A1* | 4/2007 | Flohr | ..................... | A61B 6/032 378/4 |
| 2007/0092127 A1* | 4/2007 | Grasruck | ................... | G06T 5/50 382/132 |
| 2007/0249933 A1* | 10/2007 | Krauss | ................. | A61B 5/4869 600/425 |
| 2008/0253625 A1* | 10/2008 | Schuckers | .......... | G06K 9/00114 382/125 |
| 2009/0022380 A1* | 1/2009 | Zhao | ..................... | G06T 3/4007 382/131 |
| 2009/0028287 A1* | 1/2009 | Krauss | ................... | A61B 6/032 378/4 |
| 2010/0027911 A1* | 2/2010 | Lefebvre | ............ | G06K 9/00986 382/294 |
| 2010/0104191 A1* | 4/2010 | McGwire | ............. | G06K 9/0063 382/190 |
| 2010/0128844 A1* | 5/2010 | Thomsen | ................ | A61B 6/032 378/53 |
| 2010/0135557 A1* | 6/2010 | Krauss | ................... | A61B 6/482 382/131 |
| 2010/0214291 A1* | 8/2010 | Muller | ................. | G06K 9/4604 345/420 |
| 2010/0226474 A1* | 9/2010 | Yamakawa | ............ | A61B 6/032 378/5 |
| 2010/0328313 A1* | 12/2010 | Zamyatin | ............... | G06K 9/342 345/440 |
| 2011/0274342 A1* | 11/2011 | Maeda | ............ | G01N 21/95623 382/149 |
| 2012/0250967 A1* | 10/2012 | Flohr | ....................... | A61B 6/12 382/131 |
| 2012/0281900 A1* | 11/2012 | Rueckert | ................ | G06K 9/468 382/131 |
| 2013/0077891 A1* | 3/2013 | Nimnual | ............... | G06T 7/0034 382/276 |
| 2013/0287260 A1* | 10/2013 | Taguchi | ................ | G06T 11/003 382/103 |
| 2014/0050378 A1* | 2/2014 | Sengupta | .............. | G06T 11/008 382/131 |
| 2014/0321603 A1* | 10/2014 | Taguchi | ................. | A61B 6/032 378/5 |
| 2015/0294194 A1* | 10/2015 | Znaidai | ............. | G06F 17/30253 382/190 |
| 2016/0058404 A1* | 3/2016 | Nitta | .................... | A61B 6/4241 378/5 |
| 2016/0120493 A1* | 5/2016 | Maeda | ................... | A61B 6/032 382/131 |
| 2016/0292891 A1* | 10/2016 | O'Donnell | ............ | G06T 11/001 |

FOREIGN PATENT DOCUMENTS

| | | |
|---|---|---|
| JP | 2011-206240 | 10/2011 |
| JP | 2012-245235 | 12/2012 |

OTHER PUBLICATIONS

Thorsten R.C. Johnson et al. "Dual Energy CT in Clinical Practice", Springer Link, 2011, 4 pages.

Liran Goshen et al. "An Iodine-Calcium Separation Analysis and Virtually Non-Contrasted Image Generation Obtained With Single Source Dual Energy MDCT", Nuclear Science Symposium Conference Record, 2008, 3 pages.

"Kullback-Liebler Divergence", http://en.wikipedia.org/wiki/Kullback%E2%80%93Leibler_divergence, 2014, 10 pages.

Alexander A. Zamyatin et al. "Advanced material separation technique based on dual energy CT scanning,", Proc. of SPIE vol. 7258 725844-1, 2009, 10 pages.

A. P. Dempster et al. "Maximum Likelihood from Incomplete Data via the EM Algorithm", Journal of the Royal Statistical Society. Series B (Methodological), vol. 39, No. 1. 1977, 39 pages.

Jianhua Lin "Divergence Measures Based on the Shannon Entropy", IEEE Transactions on Information Theory, vol. 37. No. 1, Jan. 1991, 7 pages.

A.P. Majtey et al. "Jensen-Shannon divergence as a measure of distinguishability between mixed quantum states" Phys. Rev. A 72,052310, 2005, 14 pages.

J. Antolin et al. "Fisher and Jensen-Shannon divergences: Quantitative comparisons among distributions. Application to position and momentum atomic densities", The Journal of Chemical Physics, 2009, 8 pages.

Thomas M. Cover et al. "Entropy, Relative Entropy and Mutual Information", Chapter 2, Elements of Information Theory, 1991, 38 pages.

Lillian Lee "Measures of Distributional Similarity", Proceedings of the ACL, 1999, 8 pages.

Todd K Moon, The Expectation Maximization Algorithm, Signal Processing Magazine, IEEE, vol. 13, Nov. 1996, 14 pages.

* cited by examiner

METHOD OF, AND APPARATUS FOR, MATERIAL CLASSIFICATION IN MULTI-ENERGY IMAGE DATA

FIELD

Embodiments described herein relate generally to a method of, and apparatus for, classifying materials in multi-energy image data, for example a method and apparatus for classifying materials in multi-energy image data based on a threshold.

BACKGROUND

Computed-tomography (CT) imaging is a widely-used form of medical imaging which uses X-rays to obtain three-dimensional image data. A CT image data set obtained from a CT scan may comprise a three-dimensional array of voxels, each having an associated intensity which is representative of the attenuation of X-ray radiation by a respective, corresponding measurement volume. The attenuation of X-ray radiation by the measurement volume may be expressed as an intensity value or CT value in Hounsfield units (HU), where 0 HU is the CT value of water.

In CT scanners, an X-ray source, which may be called an X-ray tube, is rotated around a patient. The X-ray radiation that passes through the patient is captured by an X-ray detector on the opposite side of the patient. The X-ray tube has a given peak tube voltage. X-ray photons are produced by the X-ray tube, the photons having a range of energies up to an energy corresponding to the peak tube voltage. For example, an X-ray tube at a peak tube voltage of 100 kV may produce photons with a range of energies up to 100 keV. A CT scan with a peak tube voltage of 100 kV may be described as a 100 kVp scan, where kVp stands for kilovolt peak.

Conventional CT acquisition, which may be called single-energy CT, may be performed with a peak tube voltage of, for example, 120 kV and a detector that is sensitive to the spread of X-ray energies provided by the X-ray tube.

A limitation of single-energy CT imaging may be that different materials may be indistinguishable, or difficult to distinguish, in CT imaging data if the materials have similar attenuation coefficients at the energy of the CT scan. It has been found that such difficulty in distinguishing different materials may occur particularly at peak tube voltages that may be suitable for providing good image quality, for example 120 kV. Although materials may be more distinguishable if a lower peak tube voltage is used (for example, 80 kV), the image quality at such lower energies may be poorer, as the image may be more noisy.

A dual-energy, multi-energy or spectral CT system may acquire multiple, registered images at different energy levels. For example a dual-energy CT system may acquire a first image at a peak tube voltage of 120 kV and a second image at a peak tube voltage of 80 kV. The first image may be referred to as the high-energy image (or as an image obtained from a high-energy scan) and the second image may be referred to as the low-energy image (or as an image obtained from a low-energy scan).

A dual-energy CT system may acquire the high-energy image and low-energy image simultaneously, or substantially simultaneously, such that the voxels in the first image correspond to the voxels in the second image without requiring registration of the images. The images may then be considered as a single, combined set of image data comprising, for each voxel, an intensity value for the high-energy image (which may be referred to as a high-energy intensity value) and an intensity value for the low-energy image (which may be referred to as a low-energy intensity value). Each voxel also has an associated position in the coordinate space of the images (where the coordinate space for the high-energy image may be the same as the coordinate space of the low-energy image, for example as a result of simultaneous or near-simultaneous acquisition of the images).

Dual-energy (or multi-energy or spectral) CT may be used to separate materials by using both low-energy and high-energy image intensity values. Materials that exhibit similar attenuation at one of the scan energies may exhibit differing attenuation at the other of the scan energies. In some cases, materials with attenuations that are difficult to distinguish in the high-energy image may have attenuations that are easier to distinguish in the low-energy image. At the same time, using information from both the high-energy scan and the low-energy scan rather than just using information from the low-energy scan may overcome noise issues in the low-energy scan data.

The attenuation associated with some materials may be dependent on the material concentration or density. A more concentrated sample of the material may have higher attenuation (a higher CT value in Hounsfield units) than a less concentrated sample. The attenuation in the high-energy scan may change with concentration, and the (different) attenuation in the low-energy scan may also change with concentration.

A relationship may be derived between the change in attenuation with concentration in the high-energy scan and the change in attenuation with concentration in the low energy scan. It is known that, if low-energy intensity is plotted versus high-energy intensity, points representing different material concentrations may lie along, or near, a straight line on the plot of low-energy intensity versus high-energy intensity. It is also known that the slope of the straight line may be different for different materials, that is, that different materials may have a different relationship between change in attenuation with concentration in the high-energy scan and change in attenuation with concentration in the low-energy scan. Such differences may be due to properties of the materials, for example each material's atomic number. See, for example, Thorsten R. C. Johnson, Christian Fink, Stefan O. Schonberg, Maximilian F. Reiser, *Dual Energy CT in Clinical Practice*, Secaucus, N.J.: Springer, 2011.

It is well-known to use a contrast agent to increase the intensity of blood vessels as viewed in a CT image. Contrast-enhanced CT data (usually from a single-energy CT system) may be used for diagnosis or surgical planning relating to many medical conditions. For example, contrast-enhanced CT may be used for stenosis assessment, for example stenosis assessment of the coronary, renal or carotid arteries. Contrast-enhanced CT may be used to assess circuit perfusion, for example pulmonary circuit perfusion or circuit perfusion in the liver or in the brain.

In some circumstances, contrast-enhanced CT data (in which a contrast agent is used) and non-contrast-enhanced CT data (in which no contrast agent is used) are acquired for the same subject. Contrast-enhanced CT data and non-contrast-enhanced CT data may be used to create subtraction images in which, in principle, only the contrasted areas may be present (for example, subtraction images of blood vessels). The use of both contrast-enhanced CT data and noncontrast-enhanced CT data may require at least two CT scans to be taken, one with a contrast agent and one without a contrast agent.

Accurate identification of the contrast-enhanced blood pathway may be important in many uses of contrast-enhanced CT. However, accurate identification of the contrast-enhanced blood pathway may be challenging when calcium (for example, plaque or bone) is present. Calcium may appear with a similar attenuation to a contrast agent in the blood, for example an iodine-based contrast agent in the blood. It may be difficult to reliably distinguish calcium from contrast material.

FIG. 1 is a plot of mass attenuation coefficient (in $cm^2/g$) against photon energy in keV. The CT attenuation of a material may be directly related to mass attenuation coefficient. In FIG. 1, the mass attenuation coefficient is plotted on a logarithmic scale. Mass attenuation coefficient against photon energy is plotted for three materials: iodine, calcium and water.

The change in CT attenuation of a material with different energies may be related to the Z number (atomic number) of the material. Iodine (Z=53) has its maximum attenuation at low energy and a lower attenuation at higher energies.

It may be seen that, on the plot of FIG. 1, the greatest difference between the attenuation of iodine and the attenuation of calcium may be seen at an energy of around 40 to 50 keV. A smaller difference is seen at 80 keV, and a still smaller at photon energies above 80 keV. Therefore it may be more difficult to distinguish calcium from an iodine-based contrast agent at higher energies than it is at lower energies.

The best scan energy for distinguishing calcium from iodine may be around 40 keV. However, using a scan at such a low energy may require higher currents than are preferred for scanner hardware, and lead to more noise in the image data. Therefore, a dual-energy CT scan at, for example, 80 kVp and 120 kVp may be used to aid distinction of iodine and calcium while maintaining acceptable current levels and noise performance.

A number of further issues may contribute to the difficulty of separating calcium from contrast agent. Issues such as noise, motion, contrast concentration, calcium density, object dimension, CT dose level, beam hardening and partial volume effects may cause each material to exhibit a different range of intensity values in different images, or in different parts of the same image. In this case, the materials are iodine and calcium, but similar effects may also apply to images of different materials.

Lower concentrations of contrast agents may be more difficult to distinguish from calcium than higher concentrations. However, lower concentrations of iodine may be required for certain patients, for example for patients with kidney issues.

Regions of calcium having different calcium density may produce different intensities, leading to a range of intensities for calcium.

Images taken with a lower CT dose may exhibit a greater spread of intensity values for a given material than images taken with a higher dose, and therefore make materials more difficult to distinguish. The separation performance may be strongly affected at low concentrations. However, images taken with a lower dose may be preferred in some circumstances as a lower CT dose means that the patient is exposed to less radiation.

Beam hardening is a change in the energy distribution of a CT beam as it passes through the body, such that it contains a higher proportion of higher (harder) energies. Beam hardening may be due to lower energies being absorbed first by the tissue. Beam hardening may result in different parts of an object having different intensities, even if the material is the same throughout the object.

The image may exhibit partial volume effects, in which voxels on a boundary of a first material and a second material have an intensity value that is a combination of that of the first material and that of the second material.

The above effects may lead to a given material exhibiting a different range of intensities in different images, or in different parts of the same image, adding to the difficulty of distinguishing one material from another. In some circumstances, the range of intensities of a first material (for example, calcium) in a given image may overlap with the range of intensities of a second material (for example, iodine) in that image.

BRIEF DESCRIPTION OF THE DRAWINGS

Embodiments are now described, by way of non-limiting example, and are illustrated in the following figures, in which.

DETAILED DESCRIPTION

Certain embodiments provide an apparatus for processing multi-energy image data to separate at least two types of material, the apparatus comprising a classification unit, wherein the classification unit is configured to obtain a classification of pixels or voxels belonging to the types of material based on a threshold which is adaptively changed in dependence on multi-energy intensity information associated with the pixels or voxels.

Certain embodiments provide a method for processing multi-energy image data to separate at least two types of material, comprising obtaining a classification of pixels or voxels belonging to the types of material based on a threshold which is adaptively changed in dependence on multi-energy intensity information associated with the pixels or voxels.

Figure 2:
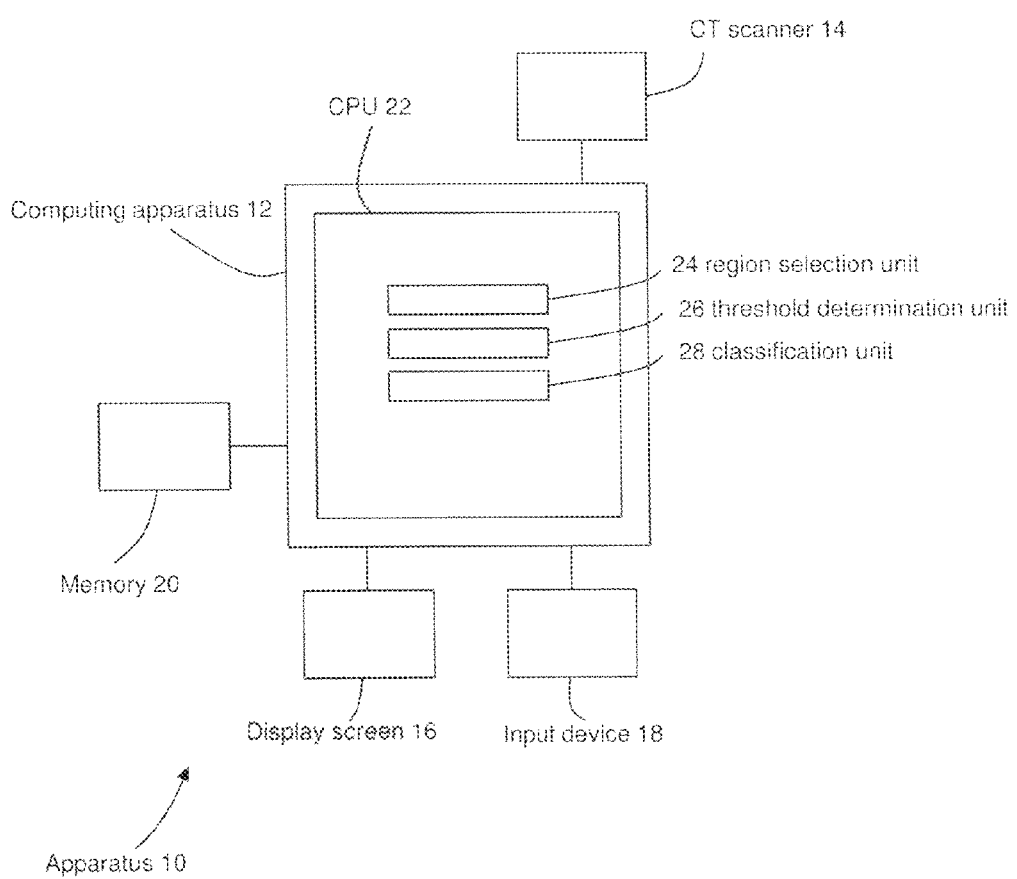
FIG. 2 is a schematic diagram of an image data processing system according to an embodiment.

An image data processing apparatus 10 according to an embodiment is illustrated schematically in FIG. 2. The image data processing apparatus 10 comprises a computing apparatus 12, in this case a personal computer (PC) or workstation, that is connected to a CT scanner 14, a display screen 16 and an input device or devices 18, such as a computer keyboard and mouse. In the present embodiment, sets of image data are obtained by the CT scanner 14 and stored in memory 20. In other embodiments, sets of image data may be loaded from a remote memory. In the present embodiment, each set of image data comprises an array of voxels. In alternative embodiments, each set of image data comprises an array of pixels.

Computing apparatus 12 provides a processing resource for classifying voxels in image data. Computing apparatus 12 comprises a central processing unit (CPU) 22 that is operable to load and execute a variety of software modules or other software components that are configured to perform the method that is described below with reference to FIG. 2.

The computing apparatus 12 includes a region selection unit 24 for selecting a region of interest in a set of image data, a threshold determination unit 26 for determining an intensity threshold in the selected region of interest, and a classification unit 28 for determining a classification based on the threshold.

In the present embodiment, the region selection unit 24, threshold determination unit 26 and classification unit 28 are each implemented in computing apparatus 12 by means of a computer program having computer-readable instructions that are executable to perform the method of the embodiment. However, in other embodiments, the various units may be implemented as one or more ASICs (application specific integrated circuits) or FPGAs (field programmable gate arrays).

The computing apparatus 12 also includes a hard drive and other components of a PC including RAM, ROM, a data bus, an operating system including various device drivers, and hardware devices including a graphics card. Such components are not shown in FIG. 2 for clarity.

Figure 1:
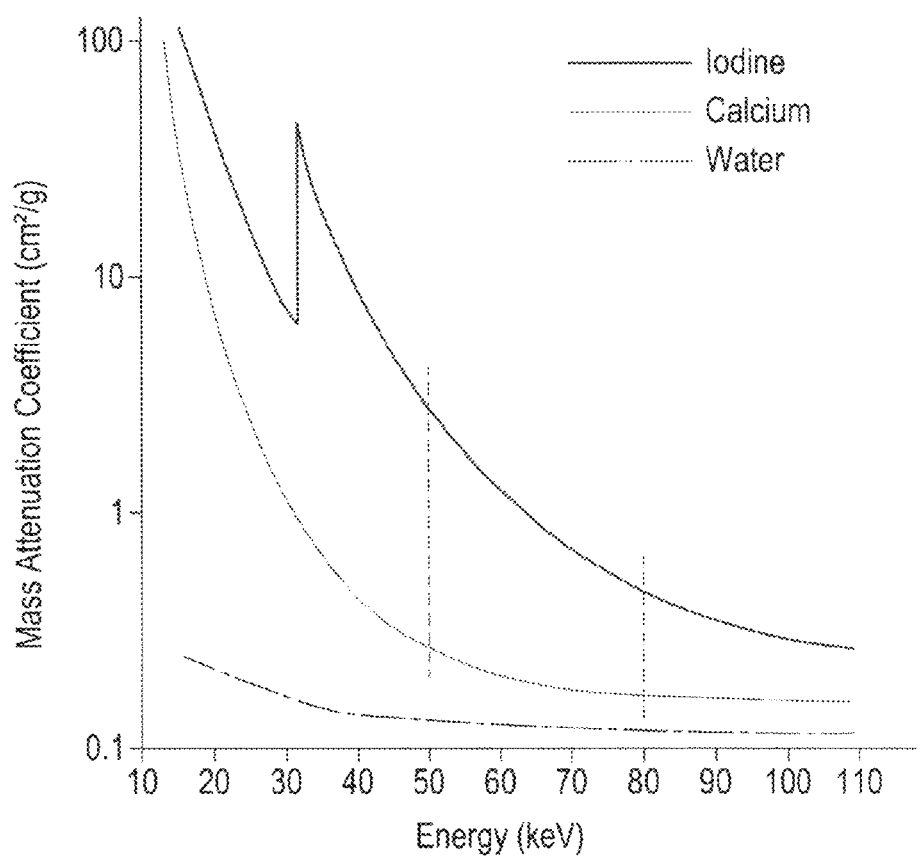
FIG. 1 is a plot of mass attenuation coefficient versus photon energy for iodine, calcium and water.
Figure 3:
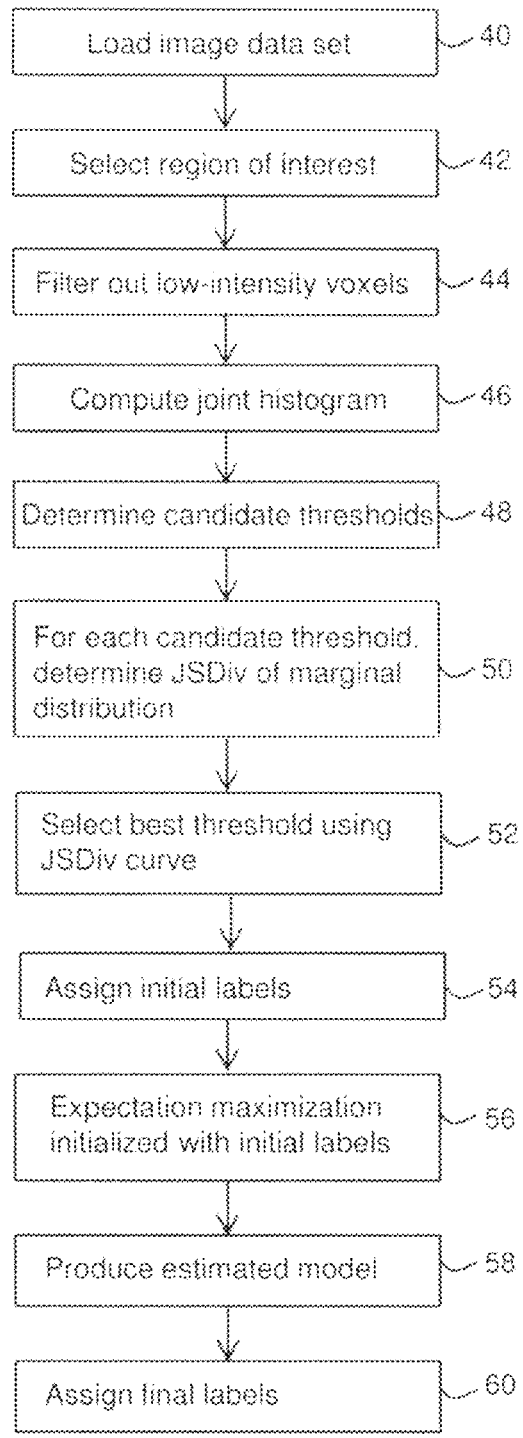
FIG. 3 is a flowchart illustrating in overview a mode of operation of an embodiment.

The system of FIG. 1 is configured to perform a series of stages as illustrated in overview in the flow chart of FIG. 3.

At stage 40 of FIG. 3, the region selection unit 24 receives from memory 20 a volumetric medical image data set 100 obtained from a dual-energy CT scan of a patient. The image data set 100 may be part of a series of DICOM (Digital Imaging and Communications in Medicine) files. In other embodiments, the region selection unit 24 receives the image data set 100 from a remote data store, for example from a server which may form part of a Picture Archiving and Communication System (PACS). In further embodiments, the region selection unit 24 receives the image data set 100 directly from the scanner 14.

In the present embodiment, the image data set 100 comprises dual-energy CT data which comprises intensities from a first CT scan of an image volume, the first CT scan having a peak tube voltage of 120 kV, and intensities from a second CT scan of the same image volume, the second CT scan having a peak tube voltage of 80 kV. As the energy of the first CT scan is higher than the energy of the second CY scan, the first CT scan may be referred to as a higher-energy scan or high-energy scan. The second CT scan may be referred to as a lower-energy scan or low-energy scan.

Each voxel in the image volume has an associated pair of intensities (IHigh, ILow) where IHigh is the intensity of the voxel in the low-energy scan (the scan at 120 kVp), and ILow is the intensity of the voxel in the low-energy scan (the scan at 80 kVp). IHigh (the intensity of the voxel in the high-energy scan) may be referred to as the high-energy intensity of the voxel. ILow (the intensity of the voxel in the low-energy scan) may be referred to as the low-energy intensity of the voxel.

In the present embodiment, the first CT scan and second CT scan are acquired simultaneously, and therefore the data from the first CT scan and the data from the second CT scan do not require registration. In other embodiments, the first and second CT scans may be acquired simultaneously, with a time offset, or sequentially. If required, data from the first CT scan and second CT scan may be registered using any appropriate registration method, in which case the image data set 100 may comprise the registered first CT scan data and second CT scan data.

Although in the present embodiment, the image data set 100 comprises dual-energy CT data, in other embodiments, the image data set 100 may comprise any image data comprising image intensities at at least two energies, for example CT image data from a multi-energy CT scan or CT image data taken with a spectral CT scanner from which data at two or more photon energies may be obtained.

In other embodiments, the image data set 100 comprises data obtained from a radiological scanner in any modality, for example CT, MRI, ultrasound, PET or SPECT.

At stage 42, the region selection unit 24 displays to a user (for example, a radiographer) an image rendered from the image data set 100. The user selects an image region in the image, for example an image region that comprises a representation of a blood vessel. The image region selected by the user may be an image region in which the user believes the both calcium and iodine may be present.

In the present embodiment, the image that is rendered from the image data set 100 and displayed to the user is a two-dimensional image representing an axial slice of the volumetric image data in image data set 100. In the present embodiment, the user selects a rectangular image region on the displayed axial slice image by clicking and dragging a mouse. In other embodiments, the user may select any two-dimensional region of the displayed axial slice image using any suitable selection method.

In further embodiments, any suitable two-dimensional or quasi-three-dimensional image may be rendered from the image data set 100 and displayed to the user, and the user may select any two-dimensional or three-dimensional image region.

In some embodiments, the user selects a two-dimensional image region from a standard MPR (multiplanar reconstruction) view (coronal, sagittal or axial). In other embodiments, the user selects a two-dimensional image region from an oblique MPR view at a user-selected angle.

In some embodiments, the displayed image is quasi-three-dimensional and the user defines a volumetric image region on the displayed image, for example by defining a three-dimensional box on the image using a mouse.

In some embodiments the displayed image is a volume rendered view. In some such embodiments, a two-dimensional or three-dimensional image region is selected using a free-moving region creation tool.

In some embodiments, the user may select the two-dimensional or three-dimensional image region in dependence on the intensity of voxels in the image region. In some embodiments, automatic or semi-automatic segmentation is performed on the image data, and the user selects the two-dimensional or three-dimensional image region in dependence on the segmentation. For example, in one embodiment, a thresholding method of segmentation is applied to the image data, and a simple slider bar control may be used to adjust the intensity threshold for segmentation. In such an embodiment, the user may use the slider bar control to segment a high intensity region, and then select that region as at least part of the two-dimensional or three-dimensional image region.

Any suitable selection method may be used to select the two-dimensional or three-dimensional image region, for example selection using a mouse, a trackball, a keyboard command, a voice command or any other suitable selection method.

The region selection unit 24 receives the user-selected image region, which in the present embodiment is a two-dimensional image region. The region selection unit 24 selects a part of the image volume in dependence on the user-selected image region.

In the present embodiment, the part of the image volume selected by the region selection unit 24 is a three-dimensional sub-volume within the image volume. The selected three-dimensional sub-volume may be called a region of interest. In the present embodiment, the three-dimensional sub-volume comprises a cuboid having x and y coordinates (coordinates in the plane of the axial slice) corresponding to the x and y coordinates of the two-dimensional image region selected by the user on the axial slice image, and a length in z (the axis perpendicular to the slice) that in determined by the region selection unit 24. In the present embodiment, the z dimension of the cuboid is centered on the axial slice on which the user selected the image region.

In the present embodiment, the length in z of the sub-volume is specified as a distance in the coordinate system of the scanner. For example, the length in z may be determined to be 30 mm. In further embodiments, the length in z of the sub-volume is specified as a number of slices, for example 10 slices. In the present embodiment, the length in z of the sub-volume is a fixed length stored in the region selection unit 24. In alternative embodiments, the length in z of the sub-volume is selected by the user, stored in the region selection unit 24, or calculated by the region selection unit 24. In one embodiment, the length in z of the sub-volume is determined by the region selection unit 24 to be the same as the length in x or length in y of the image region selected by the user. In another embodiment, the length in z of the sub-volume is determined to be a function of the length in x and the length in y of the image region selected by the user, for example an average of the length in x and length in y of the image region selected by the user.

Although in the present embodiment, the x and y coordinates of the three-dimensional sub-volume are the same as the x and y coordinates of the user-selected image region, in other embodiments, the sub-volume may be larger or smaller than the user-selected image region in x or y. For example, the sub-volume may comprise the user-selected image region plus an additional region in x and/or y. In some embodiments, the sub-volume may have any size up to and including the size of the full image volume.

Although in the present embodiment, the user selects a two-dimensional image region on a displayed two-dimensional image, in other embodiments, the user selects a three-dimensional image region on a quasi-three-dimensional rendered image. In such embodiments, the region selection unit 24 selects a three-dimensional sub-volume in dependence on the selected three-dimensional image region. The three-dimensional sub-volume may correspond to the three-dimensional image region. The three-dimensional sub-volume may be based on the three-dimensional image region. For example, the three-dimensional sub-volume may be larger than the three-dimensional image region in one or more of x, y, and z.

Although in the present embodiment, the sub-volume (region of interest) is three-dimensional, in other embodiments the sub-volume (region of interest) may be two-dimensional. For example, the sub-volume may comprise voxels on a single axial slice. Furthermore, in some embodiments, the image data set 100 may comprise two-dimensional image data, in which case the sub-volume may comprise pixels in a two-dimensional image region.

The region selection unit 24 selects a subset 110 of the image data set 100 which comprises intensity data associated with voxels within the selected sub-volume (in further embodiments, pixels within the selected sub-volume). The image data subset 110 comprises (IHigh, ILow) intensity values for each voxel in the selected sub-volume.

The region selection unit 24 passes the image data subset 110 to the threshold determination unit 26.

At stage 44, the threshold determination unit 26 applies a filter to the image data subset 110 to remove data associated with voxels that have a low intensity (a low IHigh and/or a low ILow). The filtering process of stage 44 may remove data that may be associated with voxels that represent neither calcium nor iodine, for example voxels that represent soft tissue.

In some embodiments, removing data comprises deleting data from the image data subset 110. In other embodiments, removing data does not comprise deleting data from the image data subset 110. In some embodiments, removing data comprises flagging data such that it is not used in the remainder of the process of FIG. 3.

In the present embodiment, the filter comprises a threshold value. In the present embodiment, the threshold value is 100 HU. Data for each voxel having an IHigh below the threshold value and/or an ILow below the threshold value is removed from the image data subset 110. In further embodiments, a different threshold value is used. In alternative embodiments, different threshold values are set for IHigh and for ILow.

In other embodiments, the filter comprises a threshold value for ILow only, and data for each voxel having an ILow below the threshold value is removed from the image data subset 110. In further embodiments, the filter comprises a threshold value for IHigh only, and data for each voxel for which the IHigh value is below the threshold value is removed from the image data subset 110. In other embodiments, the filter comprises a threshold value for a combination of IHigh and ILow. For example, if the sum of IHigh and ILow is below a certain value, data for the voxel having that (IHigh, ILow) value is removed from the image data subset 110.

In the present embodiment, the filter filters out voxels having (IHigh, ILow) values with an IHigh below 100 HU. In other embodiments, a different threshold value is used. In the present embodiment, the filter threshold value (100 HU) is a fixed value which is stored by the threshold determination unit 26. In other embodiments, the filter threshold value may be input or selected by the user, or may be determined by any automatic, semi-automatic or manual process. In some embodiments, the threshold value is determined empirically.

In alternative embodiments, the user may use any method to remove regions which the user does not wish to include in subsequent stages of the process of FIG. 3. For example, the user may use an interactive method for modifying the region of interest. In some embodiments, an automatic method may be used to select unwanted regions, which may or may not be based on a threshold.

By filtering the image data subset 110, intensity values associated with voxels that are unlikely to represent either calcium or iodine may be removed, and may not be used in subsequent stages of the process of FIG. 3.

In some circumstances, it may be possible to use a fixed threshold value to separate soft tissue voxels from voxels representing calcium and/or iodine, because there may be a large difference in intensity (ILow, IHigh, or both) between voxels of soft tissue and voxels of calcium and/or iodine. The range of intensities of calcium may be close to or overlapping with the range of intensities of iodine, but both the range of intensities of calcium and the range of intensities of iodine may be significantly higher than the range of intensities of soft tissue, such that a fixed threshold value may be used to remove soft tissue voxels from an image containing soft tissue, calcium and iodine.

In further embodiments, no filter is used to remove low-intensity voxels, and stage 44 is omitted. In other embodiments, a filter may be applied at any stage of the process of FIG. 3, for example before a sub-volume is selected at stage 42, or after a joint histogram is computed at stage 46.

At stage 46, the threshold determination unit 26 computes a joint histogram 200 of the (IHigh, ILow) intensity values remaining in the image data subset 110 after the filtering of stage 44. Each (IHigh, ILow) value is associated with a voxel in the sub-volume selected by the region selection unit 24 at stage 42.

Figure 4:
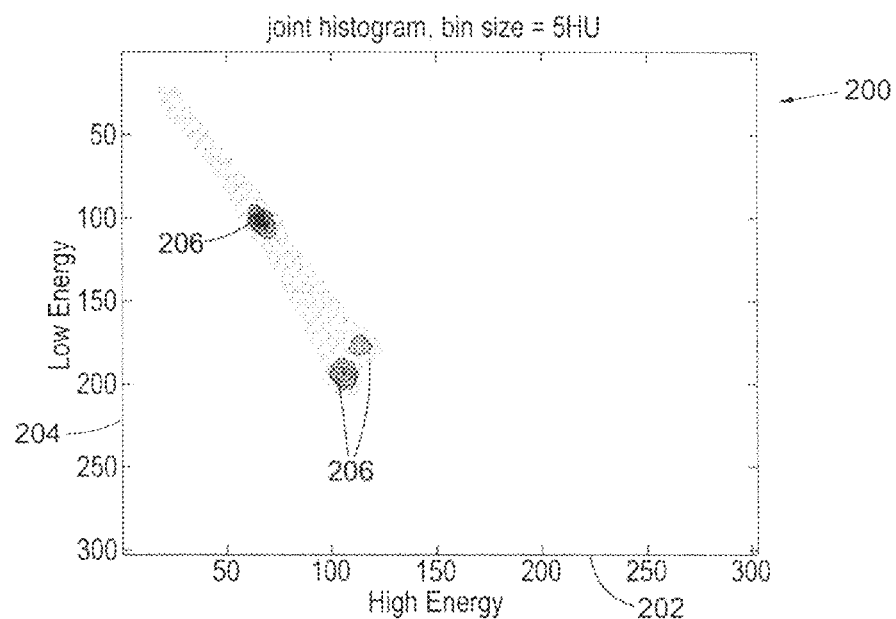
FIG. 4 is an example of a joint histogram of low-energy intensity and high-energy intensity.

An example of such a joint histogram 200 is illustrated in FIG. 4. The x axis 202 of the joint histogram 200 is IHigh, the intensity from the high-energy scan, and the y axis 204 of the joint histogram 200 is ILow, the intensity from the low-energy scan. IHigh and ILow are each measured in Hounsfield units. In alternative embodiments, the x axis may be ILow and the y axis may be IHigh.

The joint histogram 200 comprises a plurality of two-dimensional bins of equal size. Each (IHigh, ILow) value falls into a two-dimensional bin in the joint histogram 200. One may say that each voxel in the (filtered) image data subset 110 is assigned to a bin corresponding to its (IHigh, ILow) value.

In some embodiments, the number of voxels in each bin may be represented as a color. Any suitable colors may be used, which may include greyscale values. For example, in one embodiment, bins which contain few voxels are represented as blue. Bins which contain many voxels are represented as red. Bins which contain intermediate number of voxels are represented by colors on a spectrum between blue and red. In other embodiments, bins are displayed in a method other than the display with color-coded bins. In further embodiments, the joint histogram 200 is not displayed.

In FIG. 4, the number of voxels in each bin is represented by shading, with white areas of the joint histogram representing bins containing few voxels, dark shading representing bins containing many voxels, and light shading representing intermediate values.

In the present embodiment, the bin size is 5 Hounsfield units by 5 Hounsfield units. In other embodiment, any bin size may be used. In the present embodiment, the bin size is fixed and the bin size is stored in the threshold determination unit 26. In alternative embodiments, the bin size is determined by the threshold determination unit 26. For example, the bin size may be determined based on the range of intensities associated with the voxels in the subset 110. In other embodiments, the bin size is selected by the user. In further embodiments, any suitable method of determining the bin size may be used.

A large number of voxels having similar (IHigh, ILow) values may result in a cluster 206 of bins on the joint histogram 200, each bin in the cluster 206 containing a high number of voxels when compared with bins outside the cluster. For example, if the selected sub-volume contains a large number of voxels representing iodine, where the iodine has a consistent concentration, it may be expected that those voxels may form a cluster 206 of bins on the joint histogram 200.

Voxels representing different materials may form different clusters 206 on the joint histogram 200. For example, two materials whose voxels have similar intensities in the high-energy scan (similar IHigh) may have differing intensities in the low-energy scan (differing ILow) and therefore form separate clusters 206 (which may in some circumstances overlap).

It is known that different concentrations of a material may have different attenuation, and therefore that voxels representing different concentrations of the material may form clusters 206 in different regions of the (IHigh, ILow) joint histogram 200, or may form a single cluster 206 that is distributed over an extended region of the (IHigh, ILow) joint histogram 200.

It is known that the (IHigh, ILow) intensity values of voxels representing different concentrations or densities of a first material may lie on or near a first straight line in the joint histogram 200, and that the (IHigh, ILow) intensity values of voxels representing different concentrations or densities of a second material may lie along or near a second straight line in the joint histogram 200, where the second straight line is different from the first straight line. In general, (IHigh, ILow) values of voxels representing different materials may lie along different lines. The different lines may each pass through the water point, the water point being defined as (IHigh=0, ILow=0). See, for example, Thorsten R. C. Johnson, Christian Fink, Stefan O. Schonberg, Maximilian F. Reiser, *Dual Energy CT in Clinical Practice*, Secaucus, N.J.: Springer, 2011.

However, in practice, it has been found that various effects described above (for example, noise, beam hardening or partial volume effects) may cause the intensities of voxels of a particular material to spread out on the joint histogram 200, making it difficult to distinguish between voxels of a first material and voxels of a second material. Each cluster 206 may be more spread out than would otherwise be the case. In practice, the clusters 206 of different materials may overlap. Furthermore, as a result of the effects described above, the slope and/or intercept of each straight line may be different in different images, or in different regions of the same image.

The joint histogram 200 of FIG. 4 displays three clusters 206 of intensity values. One cluster 206 has (IHigh, ILow) values around (70, 100). Many voxels lie in the cluster of bins around (70, 100), so the center of the cluster around (70, 100) is colored red (represented by dark shading in FIG. 4).

Another cluster 206 has (IHigh, ILow) values of around (110, 200) and the other cluster 206 has (IHigh, ILow) values of around (120, 180).

It is expected that voxels representative of calcium may have (IHigh, ILow) values that lie on or near a first line in the joint histogram 200, that voxels representative of iodine may have (IHigh, ILow values) that lie on or near a second line in the joint histogram 200, and that it may therefore be possible to determine a line (a two-dimensional threshold) in the joint histogram 200 that approximately divides bins containing voxels of calcium from bins containing voxels of iodine. The position of the line may be different for different images. Stages 48 to 52 of the process of FIG. 3 are directed towards determining such a line, which may be called a two-dimensional threshold.

At stage 48, the threshold determination unit 26 determines a set of candidate thresholds 208. In the present embodiment, each candidate threshold 208 is a straight line on the joint histogram 200.

Although in the present embodiment, each candidate threshold 208 is a straight line, in other embodiments each candidate threshold 208 may be any appropriate function of IHigh and ILow. For example, each candidate threshold 208 may be a curved line (the line model of the present embodiment being replaced with a higher order curve model).

Figure 5:
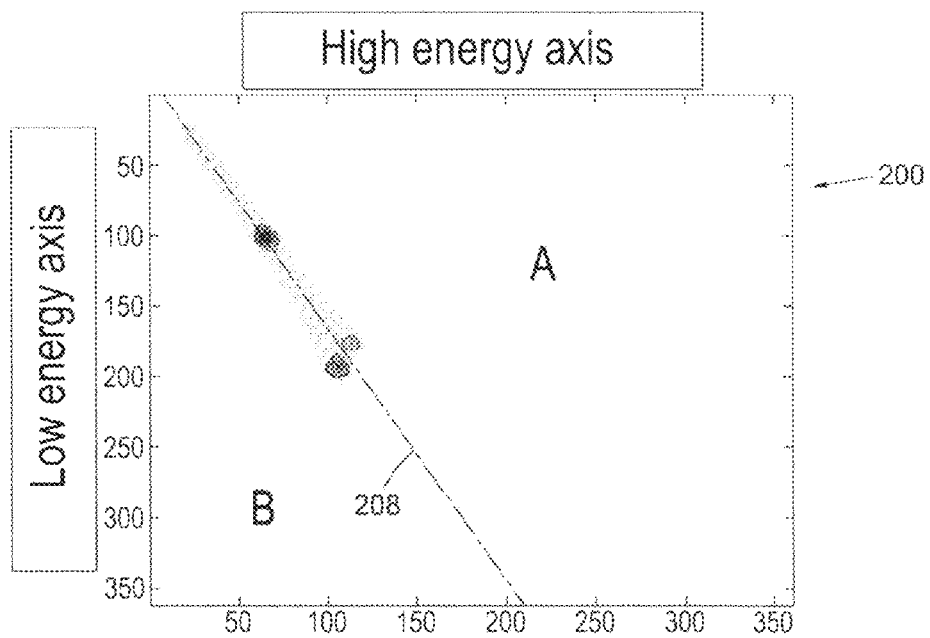
FIG. 5 is a joint histogram showing a candidate threshold.

FIG. 5 shows the joint histogram 200 of FIG. 4, on which is drawn a candidate threshold 208.

Figure 6:
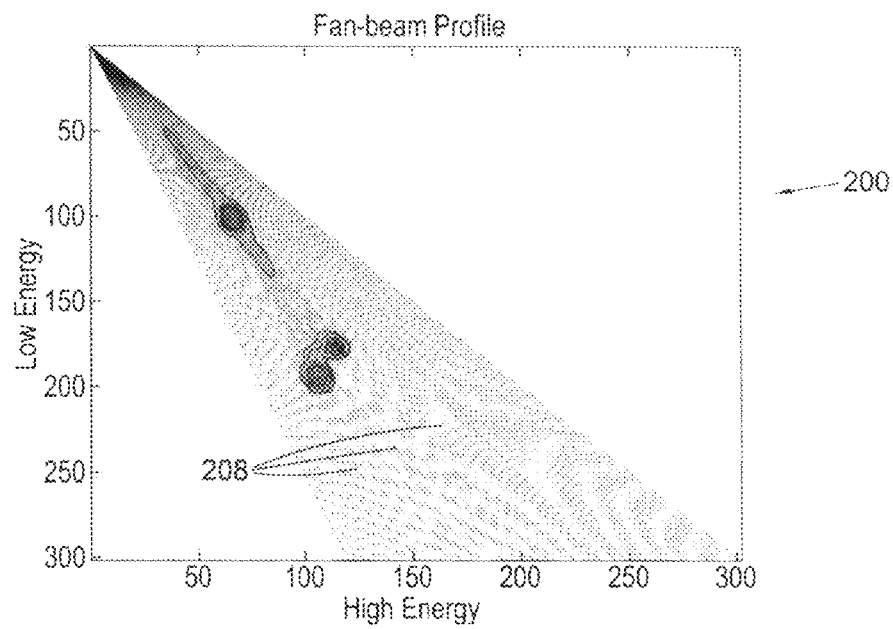
FIG. 6 is a joint histogram showing a plurality of candidate thresholds.

FIG. 6 shows a set of candidate thresholds 208, which are illustrated as a fan beam of candidate threshold lines 208. In the present embodiment, each candidate threshold 208 is a straight line with an intercept at (0,0), but each of the candidate threshold lines 208 has a different slope.

In the present embodiment, the slope of each candidate threshold 208 may be expressed as a ratio of IHigh/ILow. The range of slopes in the present embodiment is from 0.4 to 1 with an increment of 0.01. In alternative embodiments, the slope and/or the increment between the slopes may be expressed as a ratio of ILow/IHigh, as an angle, or using any other suitable method.

In the present embodiment, each candidate threshold 208 is a line with an intercept at (0,0). In other embodiments, some or all of the candidate thresholds 208 may have a different intercept.

In other embodiments, the set of candidate thresholds 208 may have a different range of slopes or a different increment in slope between adjacent candidate thresholds 208 from the set of candidate thresholds 208 shown in FIG. 6. In some embodiments, the candidate thresholds 208 are equally spaced in angle or equally spaced in slope. In other embodiments, the candidate thresholds 208 are not equally spaced. In some embodiments, the range of slopes may be greater or less than the range of slopes of the candidate thresholds 208 shown in FIG. 6. In some embodiments, the range of slopes may extend across the entire histogram.

In some embodiments, the slope and/or intercept of one or more of the candidate thresholds 208 and/or an increment between the slopes of the candidate thresholds 208 may be determined by a user, for example determined manually by a user. For example, the user may define a central candidate threshold 208, a range of candidate thresholds 208 or an increment between candidate thresholds 208.

In some embodiments, the range of slopes, intercept of some or all of the lines and/or increment between the slopes may be determined semi-automatically or automatically by the threshold determination unit 26. For example, a range of slopes, or an increment in angle or slope between candidate thresholds 208 may be determined in dependence on the spread of (IHigh, ILow) intensity values in the joint histogram 200. In some embodiments, the range of slopes, intercept of some or all of the lines and/or increment between the slopes may be pre-determined and stored in threshold determination unit 26.

In some embodiments, the range of slopes, intercept, or increment between slopes of the candidate thresholds 208 may be determined using prior knowledge. Such prior knowledge may comprise, for example, the results of the process of FIG. 3 when performed on other image data or other sub-volumes within the same image data.

At stage 50, the threshold determination unit 26 performs an iterative process on the candidate thresholds 208 determined by the threshold determination unit at stage 48.

The threshold determination unit 26 selects a first candidate threshold 208, for example the candidate threshold 208 that is illustrated in FIG. 5. The threshold determination unit 26 partitions the joint histogram 200 into a first region A which is above the candidate threshold 208, and a second region B which is below the candidate threshold 208, as illustrated in FIG. 5.

In the present embodiment, the region A of the joint histogram 200 that is above the threshold 208 is the region of greater High and lower ILow than the candidate threshold line 208. A point in region A has greater IHigh and/or lower ILow than the nearest point on the candidate threshold line 208. The region B of the joint histogram 200 that is below the candidate threshold line 208 is the region of greater ILow and lower IHigh than the candidate threshold line 208. A point in region B had greater ILow and/or lower IHigh than the nearest point on the candidate threshold line 208.

In alternative embodiments, the axes of the joint histogram 200 may be drawn differently, for example with (0,0) in the lower left corner of the joint histogram 200. In such embodiments, region A may be the region below the line (but still the region of greater IHigh and lower ILow) and region B may be the region above the line (but still the region of greater ILow and lower IHigh).

Each of region A and region B comprises a group of voxels (the voxels in bins in that region). The (IHigh, ILow) intensities of the group of voxels in region A form a first two-dimensional distribution of intensities. The (IHigh, ILow) intensities of the group of voxels in region A form a second two-dimensional distribution of intensities.

For the first candidate threshold 208, the threshold determination unit 26 calculates a metric which represents a statistical dissimilarity between the distribution of the (IHigh, ILow) values of voxels in bins in region A and the distribution of the (IHigh, ILow) values of voxels in bins in region B. In alternative embodiments, any suitable method of determining a statistical dissimilarity between the distributions may be used. Determining a statistical dissimilarity between the two-dimensional (IHigh, ILow) distributions may comprise determining a statistical dissimilarity between one-dimensional distributions derived from or associated with the two-dimensional distributions, as described below.

In some embodiments, the threshold determination unit 26 may determine any probability distribution distance metric which calculates a mutual statistical dependence between two distributions to be compared. Different quantities that may be used individually or in combination to form a metric may comprise Jensen-Shannon divergence, mutual information, or entropy (marginal or joint).

In the present embodiment, the threshold determination unit 26 determines a marginal distribution of low-energy intensity for the voxels in bins in region A and a marginal distribution of low-energy intensity for the voxels in bins in region B.

Determining the marginal distribution for region A comprises obtaining a one-dimensional distribution (one-dimensional histogram) of the ILow values of the voxels in bins in region A. Determining the marginal distribution for region A may comprise projecting the (IHigh, ILow) values in region A of the joint histogram 200 onto the low-energy (ILow) axis of the joint histogram 200. The resulting marginal distribution is a one-dimensional histogram which may be displayed on a plot having ILow in Hounsfield units on the x axis and number of voxels on the y axis. In the present embodiment, the one-dimensional histogram has the same ILow bin size as the joint histogram. When the joint histogram 200 of FIG. 4 is projected onto the ILow axis, three peaks may be seen in the resulting one-dimensional histogram, two of which are close together in ILow.

Determining the marginal distribution for region B comprises obtaining a one-dimensional distribution (one-dimensional histogram) of the ILow values of the voxels in bins in region B. Determining the marginal distribution for region B may comprise projecting the (IHigh, ILow) values in region B of the joint histogram 200 onto the low-energy (ILow) axis of the joint histogram 200.

The threshold determination unit 26 determines the Jensen-Shannon divergence of the marginal distribution for region A and the marginal distribution for region B (where region A and region B are the regions respectively above and below the first candidate threshold 208).

If the marginal distribution for region A and the marginal distribution for region B are similar then the Jensen-Shannon divergence of the two marginal distributions may be small. Similar marginal distributions may indicate that the same material is present in both regions.

If the marginal distribution for region A and the marginal distribution for region B are dissimilar, then the Jensen-Shannon divergence of the two marginal distributions may be larger. Dissimilar distributions may indicate that different materials are present in each region.

Once the threshold determination unit 26 has determined the Jensen-Shannon divergence of the marginal distributions for the first candidate threshold 208, the threshold determination unit 26 selects a second candidate threshold 208.

The threshold determination unit 26 partitions the joint histogram 200 into two regions, region A and region B, according to the second candidate threshold 208. If the first and second candidate thresholds 208 have different slope and/or intercept then the region A and region B for the second candidate threshold 208 are different from the region A and region B for the first candidate threshold 208.

The threshold determination unit 26 determines a marginal distribution for region A comprising the ILow values of voxels in the bins in region A. The threshold determination unit 26 determines a marginal distribution for region B comprising the ILow values of voxels in the bins in region B. The threshold determination unit 26 determines the Jensen-Shannon divergence of the marginal distribution for region A and the marginal distribution for region B, where region A and region B are the regions respectively above and below the second candidate threshold 208.

The threshold determination unit 26 repeats the process of selecting a further candidate threshold 208, partitioning the joint histogram 200 into regions A and B in accordance with the candidate threshold 208, determining a marginal distribution for region A and a marginal distribution for region B and determining a Jensen-Shannon divergence for the marginal distributions of region A and region B until a Jensen-Shannon divergence has been determined for each of the candidate thresholds 208.

The Jensen-Shannon divergence is a metric for estimating the similarity between two probability distributions (See Jianhua Lin, 'Divergence measures based on the Shannon Entropy', IEEE Transactions on Information Theory, vol. 37, no. 1, January 1991). The Jensen-Shannon divergence is a linear combination of Kullback-Leibler divergences. The Kullback-Leibler divergence is a statistic for distance between distributions, but the Kullback-Leibler divergence can have infinite values and is not symmetric. Therefore the Kullback-Leibler divergence may not be able to be used as a metric directly. The Jensen-Shannon divergence, by contrast, is symmetric and finite and is suitable to be used as a metric.

The Jensen-Shannon divergence of two distributions, P and Q, may be defined by the following equation:

$$JSD(P\|Q) = \frac{1}{2} D(P\|M) + \frac{1}{2} D(Q\|M)$$

where

P and Q are the two probability distributions to be compared;
JSD(P∥Q) is the Jensen-Shannon divergence of P and Q;
M=½(P+Q), where M is the average probability distribution of P and Q. M is used as a reference distribution to which the Kullback-Leibler divergence of distribution P and distribution Q are calculated;
D(D∥M) is the Kullback-Leibler divergence distance between distribution P and distribution M;
D(Q∥M) is the Kullback-Leibler divergence distance between distribution Q and distribution M.

The Jensen-Shannon divergence metric bounds are 0≤JSD (P∥Q)≤1.

For each candidate threshold 208, the marginal histogram derived for region A (the region above the candidate threshold 208) may be denoted as MargHist_A and the marginal histogram derived for region B (the region below the candidate threshold 208) may be denoted as MargHist_B. The Jensen-Shannon divergence of the marginal distribution for region A and the marginal distribution for region B is:

$$JSD(\text{MargHist\_}A \| \text{MargHist\_}B) = \frac{1}{2} D(\text{MargHist\_}A \| M) + \frac{1}{2} D(\text{MargHist\_}B \| M)$$

Where M=½(MargHist_A+MargHist_B)

In the present embodiment, each candidate threshold 208 has an associated slope S, all candidate thresholds 208 having a common intercept at (0,0).

The threshold determination unit 26 determines a Jensen-Shannon divergence for each candidate threshold 208, which may be described as determining a Jensen-Shannon divergence for each slope S in the range of slopes represented by the candidate thresholds 208.

At stage 52, the threshold determination unit 26 plots Jensen-Shannon divergence against slope S for each of the candidate thresholds 208, thereby obtaining a plot of Jensen-Shannon divergence against slope for the range of slopes of the candidate thresholds 208.

Figure 7:
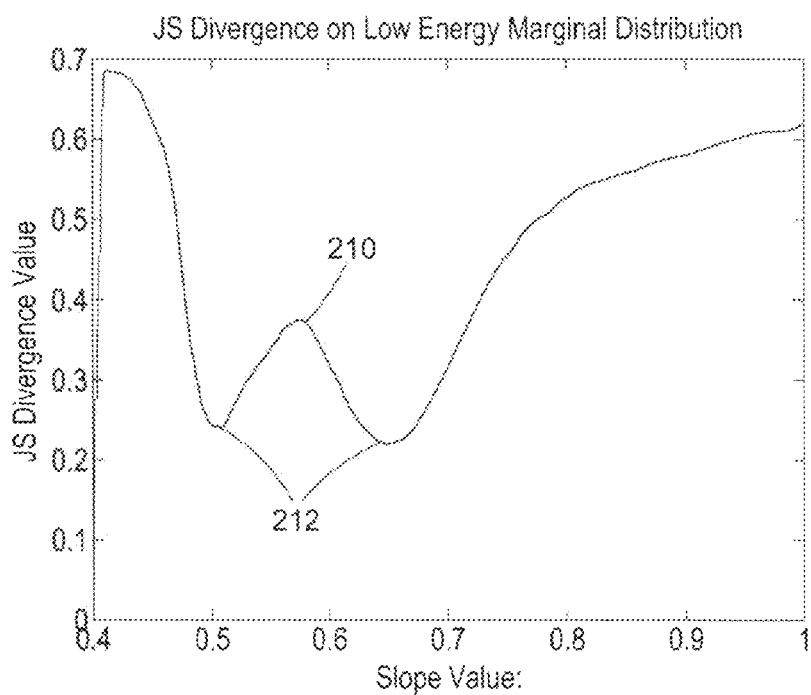
FIG. 7 is a plot of Jensen-Shannon divergence versus threshold slope.

An example of a plot of Jensen-Shannon divergence versus slope is shown in FIG. 7. Although in FIG. 7, the plot is shown as if displayed on a screen, in many embodiments the plot of Jensen-Shannon divergence against slope is calculated by the threshold determination unit 26 but is not displayed.

The threshold determination unit 26 determines whether the plot of Jensen-Shannon divergence against slope contains a local maximum between two local minima.

If the plot of Jensen-Shannon divergence against slope does not contain a local maximum between two local minima, the threshold determination unit 26 determines that the region of interest for which the process of FIG. 3 is performed contains only one of the materials of interest (in this embodiment, calcium or iodine). All of the voxels in the region of interest that are plotted on the joint histogram 200 are assigned to one class.

For example, a volume imaged in a standard dual-energy CTA (Carotid Angiography or Coronary Angiography) study may always have a large amount of contrast agent but may not always have calcium present. A perfectly healthy person may not have any calcium in the blood vessels. In such a case, a region of interest comprising a representation of a blood vessel may be found to contain only iodine and not calcium. Therefore, if all voxels of the joint histogram 200 are determined to be in a single class, that class may be determined to be iodine. The classification unit 28 labels all voxels in the joint histogram 200 as iodine.

If the plot of Jensen-Shannon divergence against slope contains a local maximum between two local minima, the threshold determination unit 26 identifies the candidate threshold 208 corresponding to the local maximum between the two minima.

For example, the plot of FIG. 7 includes a local maximum 210 between two local minima 212. The Jensen-Shannon divergence is high in the low-slope and high-slope regions of the plot.

In FIG. 7, the Jenson-Shannon divergence drops off at the very lowest slope value. This is a result of a zero value for Jensen-Shannon divergence being assigned to a situation where one of the two marginal distributions is empty. In alternative implementations, a very high Jensen-Shannon divergence may be assigned when one of the two marginal distributions is empty. The zero value for Jensen-Shannon distribution in FIG. 7 is not considered to be a local minimum 212, but instead is a feature of the particular implementation of the Jensen-Shannon plot.

High values of Jensen-Shannon divergence at high and low slope may be because a candidate threshold 208 with a slope near the edge of the plot (for example a slope near 0.4 or a slope near 1) may divide the joint histogram 20 into a first region containing all, or nearly all, of the intensities of voxels representing calcium and also containing all, or nearly all, of the intensities of voxels representing iodine, and a second region that does not contain any, or many, intensities of voxels representing either calcium or iodine. The distributions between the first region and second region will be dissimilar and therefore the Jensen-Shannon divergence will be high.

A candidate threshold 208 that has a slope which corresponds to a minimum on the plot of Jensen-Shannon divergence against slope (in FIG. 7, a slope of around 0.5 or 0.65) may divide the joint histogram 200 into two regions that each contain many voxels representing calcium, or two regions that each contain many voxels representing iodine. Therefore the distributions in the two regions may be similar, and the Jensen-Shannon divergence may be low.

Figure 8:
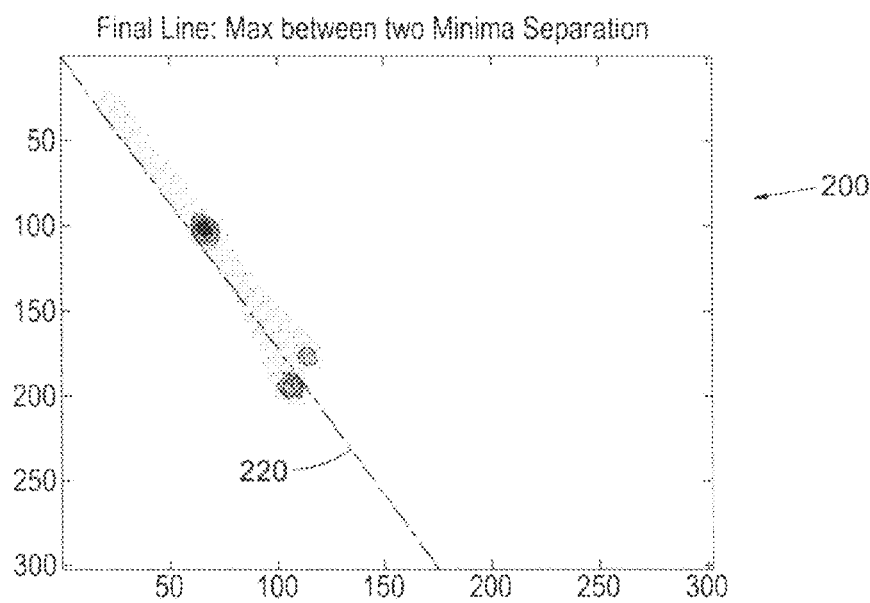
FIG. 8 is a joint histogram showing a determined threshold.
Figure 9:
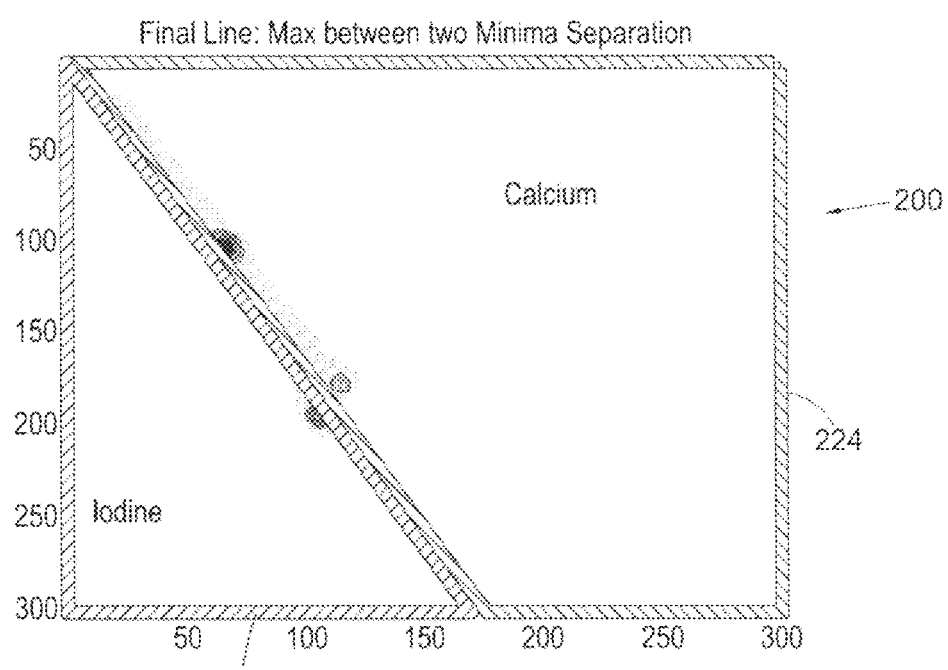
FIG. 9 is a joint histogram showing regions of initial labeling as calcium and iodine.

The candidate threshold 208 for which the Jensen-Shannon divergence has a local maximum is determined to be the candidate threshold 208 that most effectively separates calcium from iodine. This is the line that separates the distributions such that they have the least dependency between them. The threshold determination unit 26 selects the candidate threshold with a slope corresponding to the local maximum, which in FIG. 7 is the candidate threshold with a slope of 0.58. The selected threshold 220 is plotted on the joint histogram 200 of FIG. 8. A division of the joint histogram 200 into a calcium region having a boundary 224 and an iodine region having a boundary 226 is illustrated in FIG. 9. In this embodiment, the division made using the selected threshold 220 is an approximate division, approximately separating calcium from iodine. The division made using the selected threshold 220 is refined in subsequent stages of the process of FIG. 3.

In the present embodiment, the selected threshold 220 is one of the candidate thresholds 208. In other embodiments, the selected threshold 220 may not be one of the candidate thresholds 208. For example, the selected threshold 220 may be a line with a slope that lies between the slopes of two calculated candidate thresholds 208. For example, a curve may be fitted to the plot of Jensen-Shannon divergence versus slope, and the maximum of the curve may occur at a slope value that was not a slope value used for one of the candidate thresholds 208. The selected threshold may have the slope value of the maximum of the curve.

At stage 54, the threshold determination unit 26 passes the selected threshold 220 to the classification unit 28. The classification unit 28 labels voxels having (IHigh, ILow) values in the region 224 above the selected threshold 220 as calcium. The classification unit 28 labels voxels having (IHigh, ILow) values in the region 226 below the selected threshold 220 as iodine.

The labels applied by the classification unit 28 at stage 54 of the process of FIG. 3 may be described as initial labels. The initial labels applied by the classification unit 28 may not provide an accurate determination of the material of each voxel. Rather, the initial labels may provide a rough separation of calcium and iodine which may approximate the correct material labeling. The initial labels constitute a binary, non-probabilistic labeling in which each voxel represented in the joint histogram 200 is labeled either as calcium or as iodine.

Stages 46 to 54 of the process of FIG. 3 may provide an approximate labeling of calcium and iodine in the region of interest. Stages 46 to 54 may provide an initial separation of calcium and iodine which may then be refined in further stages of FIG. 3. Stages 46 to 54 may be described collectively as first stage in a process to separate calcium and iodine, the first stage comprising an unsupervised parametric separation.

At stage 56, the classification unit 28 uses an expectation maximization (EM) algorithm to refine the labeling of stage 54 to estimate models for each of calcium and iodine. An expectation maximization (EM) algorithm is described by T K Moon in 'The expectation maximization algorithm', *Signal Processing Magazine*, IEEE, vol. 13, pages 47-60, November 1996.

The EM algorithm used in the embodiment of FIG. 3 is an iterative cluster model estimation algorithm. It estimates model parameters by finding the maximum likelihood estimates of parameters in a statistical model.

In the present embodiment, the EM algorithm assumes that the distribution of each of calcium and iodine on the joint histogram is Gaussian. The EM algorithm therefore determines a Gaussian model for calcium intensities, and a Gaussian model for iodine intensities. A Gaussian model may be represented by an ellipse on the joint histogram.

In the present embodiment, in which the distributions are assumed to be Gaussian, the model parameters estimated by the Expectation Maximization algorithm comprise a mean and covariance matrix for the Gaussian distribution for each material. In other embodiments, the distributions may not be assumed to be Gaussian.

In further embodiments, different model estimation algorithms may be used at stage 56 to refine the binary labeling of stage 54. In some embodiments, any cluster fitting algorithm may be used. Any data clustering algorithm may be used, for example a hard partition based clustering algorithm, a fuzzy partition based clustering algorithm, a distribution based clustering algorithm, or a density based clustering algorithm. A hard partition based clustering algorithm may comprise, for example, a K-means algorithm or a variant of a K-means algorithm. A fuzzy partition based algorithm may comprise, for example, fuzzy C-means or soft K-means. A distribution based clustering algorithm may comprise, for example, a Gaussian mixture model clustering with an expectation maximization algorithm or a non-Gaussian mixture model clustering with an expectation maximization algorithm. A density based clustering algorithm may comprise, for example, DBSCAN (density based spatial clustering of applications with noise) or OPTICS (ordering points to identify the clustering structure).

In the present embodiment, the expectation maximization algorithm uses position information for each voxel (x, y, z coordinates in the coordinate space of the image data) in addition to high-energy intensity and low-energy intensity values (IHigh, ILow) for each voxel. Iodine and calcium may be assumed to be well-contained in spatial regions. In such circumstances, position proximity may be a useful means of separating iodine and calcium.

The EM algorithm is initialized using the binary labels obtained at stage 54. It has been found that, for some embodiments, initialization using the binary labels from stage 54 may provide more consistent results than initialization using other methods, for example initialization using random grouping.

In the present embodiment, the EM algorithm produces Gaussian models. When plotted on the joint histogram 200, each Gaussian model appears as an ellipse. Therefore the EM model estimates an ellipse for calcium and an ellipse for iodine. The ellipse for calcium may overlap with the ellipse for iodine on the joint histogram 200.

In the present embodiment, the EM algorithm does not estimate the number of classes in the data. In the present embodiment, the EM algorithm treats the classification as a fixed two class problem (iodine as a first class, and all possible densities of calcium as a second class), because intensities of calcium voxels are expected to lie along a first line in the joint histogram 200, and intensities of iodine voxels are expected to lie along a second, different line in the joint histogram 200. In the present embodiment is expected that the separation is only concerned with separating iodine and calcium, with voxels of soft tissue having been filtered out at stage 44. The EM algorithm estimates only the number of classes asked for.

The output of the EM algorithm is probabilistic. In the present embodiment, for each voxel, the classification unit 28 uses the EM algorithm to determine a probability that the voxel is calcium and a probability that the voxel is iodine. In other embodiments, each probability may be expressed as a likelihood or a confidence level.

In further embodiments, any suitable algorithm may be used in place of the EM algorithm. In some embodiments, each cluster is fitted to an alternative distribution rather than to a Gaussian.

Figure 10:
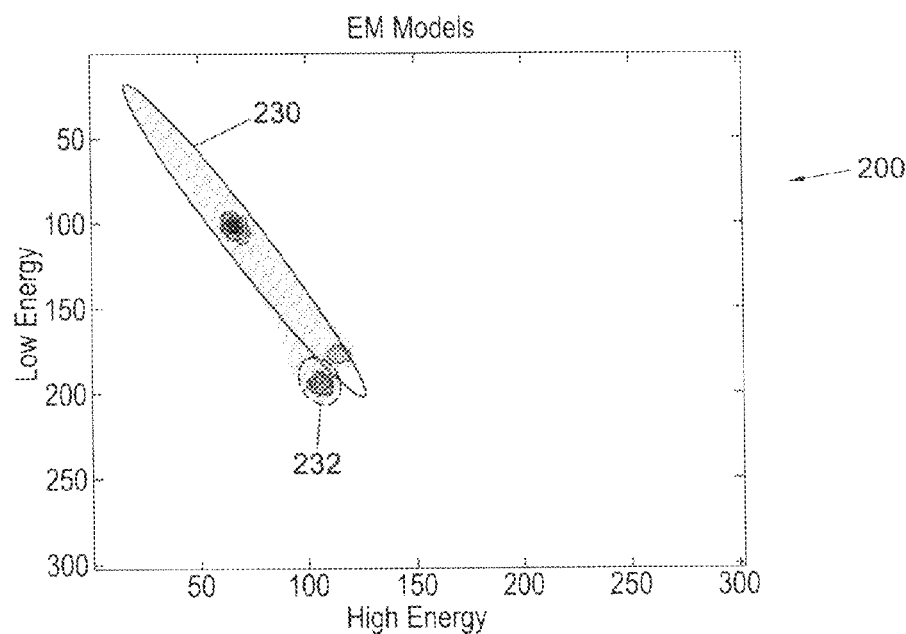
FIG. 10 is a joint histogram showing elliptical regions determined through expectation maximization.

FIG. 10 shows the joint histogram 200 of FIG. 4, on which are drawn a first ellipse 230, the first ellipse 230 defining a boundary of a region of the joint histogram 200 in which the EM algorithm has determined voxels of calcium to be present, and a second ellipse 232, the second ellipse 232 defining a boundary of a region of the joint histogram 200 in which the EM algorithm has determined voxels of iodine to be present.

It may be seen that in FIG. 10 the first ellipse 230 and the second ellipse 232 overlap. Therefore there is a region (the overlap of the first ellipse 230 and second ellipse 232) which has mixed membership of calcium and iodine voxels.

At stage 58, the classification unit 28 labels each voxel with a probability of calcium and a probability of iodine according to the results of the expectation maximization algorithm.

In the present embodiment, the labels obtained at stage 58 are the final labels output by the classification unit 28. In other embodiments, further stages may be added to the process of FIG. 3.

In some embodiments, the probabilistic labels output at stage 58 are separated into two classes of voxels in dependence on a probability threshold. One of the two classes of voxels is labeled as iodine and one of the two classes is labeled as calcium. For example, in some embodiments, voxels with a higher probability of being iodine than of being calcium are labeled as iodine, and voxels with a higher probability of being calcium than of being iodine are labeled as calcium.

In some embodiments, connected component analysis is performed on voxels after each voxel is labeled as iodine or as calcium. Connected component analysis may be used to clean up the labeling of the voxels. For example, if a single voxel of calcium is surrounded by voxels of iodine, connected component analysis may determine that the single calcium voxel should be relabeled as iodine. Connected component analysis may lead to relabeling of single and/or isolated voxels of calcium or of iodine in dependence on their surrounding voxels.

Figure 11:
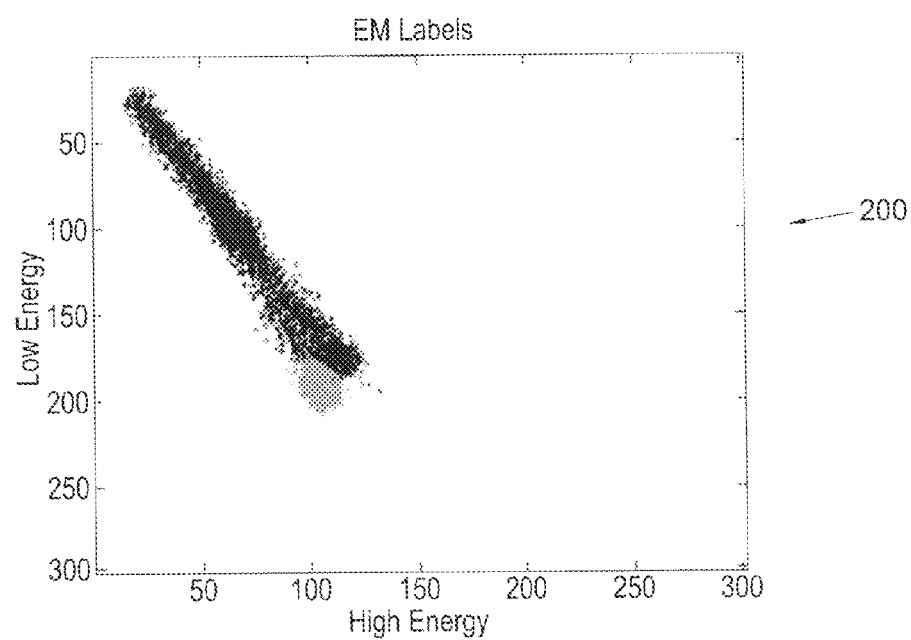
FIG. 11 is a joint histogram showing refined calcium and iodine labels.

FIG. 11 shows a joint histogram plot with a different representation of (IHigh, ILow) intensities for each voxel than is used in FIGS. 4 to 6 and FIGS. 8 to 10. In FIG. 11, for each voxel that has been labeled as calcium, a dark grey marker is placed on the (IHigh, ILow) bin associated with that voxel. For each voxel that has been labeled as iodine, a light grey marker is placed on the (IHigh, ILow) bin associated with that voxel. Therefore the colors in FIG. 11 represent the labeling of voxels in each bin, rather than the number of voxels in each bin. Voxels that have been labeled as calcium by the classification unit at stage 54 are marked in dark grey. Voxels that have been labeled as iodine by the classification unit at stage 54 are marked in light grey. White areas of the plot do not contain labeled voxels.

Figure 12:
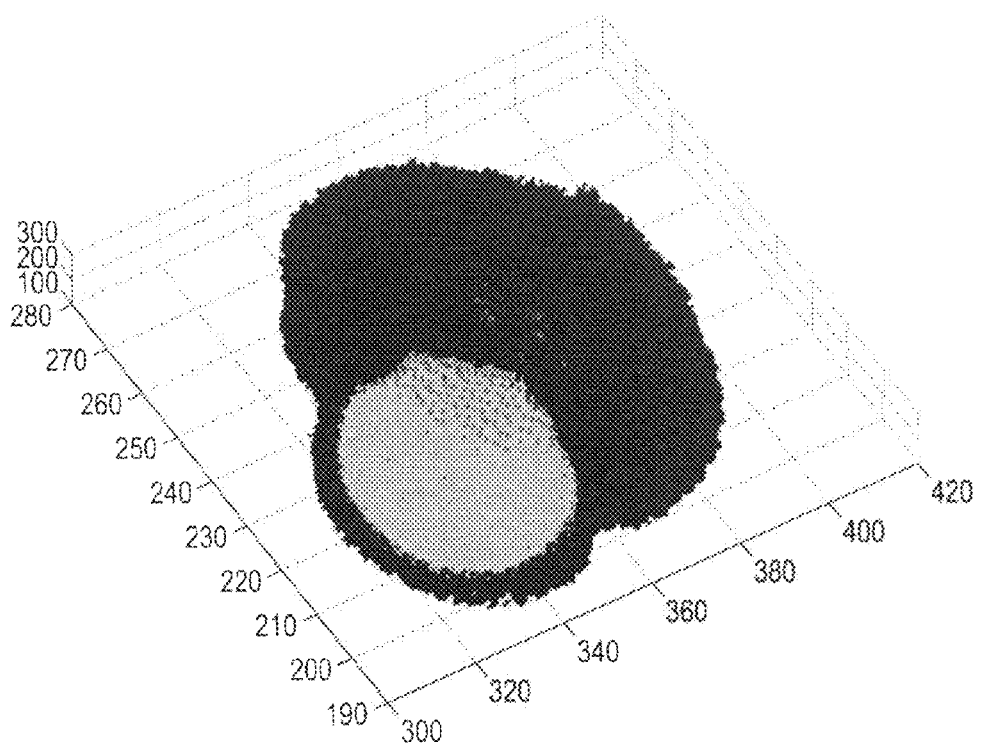
FIG. 12 is a three-dimensional plot of a region of interest, showing segmentation into calcium and iodine.

FIG. 12 is a spatial representation of the labeling information shown in FIG. 11. Each voxel in the three-dimensional space of the plot of FIG. 11 that has been labeled as calcium is colored in dark grey. Each voxel that has been labeled as iodine is colored in light grey.

The labeling of voxels shown in FIG. 12 may be considered to be a segmentation of calcium and iodine in the region of interest represented in FIG. 12.

In some embodiments, the probabilistic labels obtained in the process of FIG. 3 may be used directly to separate iodine voxels from calcium voxels of multiple calcium densities in, for example, carotid angiography, coronary angiography, or any other angiography study in which contrast is to be separated from calcium.

In some embodiments, the process of FIG. 3 may be used indirectly as a tool for image analysis (IA) algorithms for applications such as vessel tracking or lumen segmentation.

In some embodiments, the iodine labels obtained from the process of FIG. 3 may be used in the generation of a virtual non-contrast-enhanced image. A virtual non-contrast-enhanced image may be a contrast image in which voxels which have been identified as iodine are replaced with voxels having intensities representative of blood (blood without a contrast agent present). By generating a virtual non-contrast image from contrast image data, it may be possible to avoid having to take two scans, one with a contrast agent and one without, and the radiation dose experienced by the patient may be reduced accordingly.

The process of FIG. 3 may not use any pre-determined parameters or fixed thresholds, or may not use any pre-determined parameters or fixed thresholds other than the filter value of stage 44 and/or a determination of processing parameters such as bin sizes. In some embodiments, the process of FIG. 3 may have a relatively fast and simple implementation.

Figure 13:
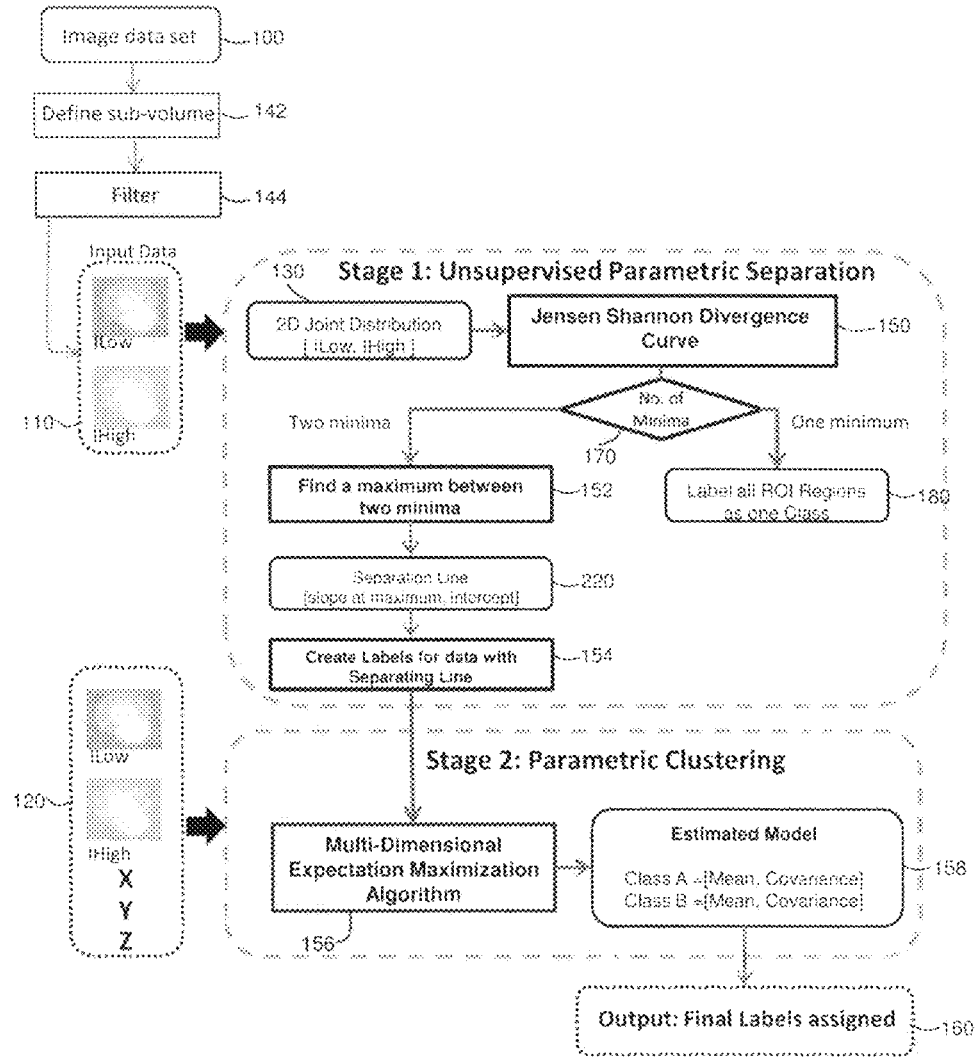
FIG. 13 is a further flowchart illustrating in overview a mode of operation of an embodiment.

The process of the flowchart of FIG. 3 may also be summarized with reference to the flowchart of FIG. 13. (Some stages of FIG. 3 are not shown explicitly in FIG. 13.)

A two-stage algorithm is performed on a region of interest of dual-energy CT image data from a dual-energy CT scan comprising a high-energy scan and a low-energy scan. Each voxel of the region of interest has an intensity IHigh from the high-energy scan, an intensity ILow from the low-energy scan, and a set of coordinates in the coordinate space of the scans.

The region selection unit 24 receives from memory 20 a set of image data 100. At stage 142, the region selection unit 24 selects a three-dimensional sub-volume (region of interest) in response to user input and selects a subset 110 of the image data 100 corresponding to the sub-volume. At stage 144, the threshold determination unit 26 applies a filter to remove low-intensity voxels from the subset 100. A subset 110 of the image data, comprising (IHigh, ILow) intensity values for each voxel in the subset, is passed to a first stage of the algorithm.

The first stage of the algorithm comprises an unsupervised parametric separation of voxels in the region of interest based only on the intensity data (IHigh and ILow) for each voxel and not on the coordinates of each voxel.

The threshold determination unit 26 determines a two-dimensional joint distribution 130 of the (ILow, Nigh) values of the subset. At stage 150, the threshold determination unit 26 determines a Jensen-Shannon divergence curve by calculating the Jensen-Shannon divergence for each of a number of candidate thresholds 208, each with a different slope.

At stage 170, the threshold determination unit 26 determines how many minima are present in the Jensen-Shannon divergence curve. If only one minimum is present, the classification unit 28 moves to stage 180, labeling all voxels in the region of interest as one class (for example, iodine).

If two minima are present, at stage 152 the threshold determination unit 26 finds a maximum between the two minima. The threshold determination unit 26 determines a separation line 220 having a slope corresponding to the maximum of the Jensen-Shannon divergence curve of stage 150. At stage 154, the classification unit 28 creates initial labels for voxels in the subset in dependence on the separation line 220.

The second stage of the algorithm comprises parametric clustering. The classification unit 28 receives a subset 120 of the image data. The subset 120 comprises intensity data for the same voxels as are in subset 110, and also contains position information (x, y, z coordinates) for each of the voxels that are in subset 110.

The classification unit 28 applies a multi-dimensional Expectation Maximization algorithm to the subset 120, using the initial labels determined at stage 154 to initialize the algorithm. The EM algorithm uses spatial information in addition to intensity information. The EM algorithm results in an estimated model 158 for each class (calcium or iodine) which is a Gaussian model having a mean and covariance. At stage 160, the classification unit 160 assigns final, probabilistic labels to the voxels in subset 120. The output is a probabilistic membership, where each data point (voxel intensity pair) is given a probability of belonging either to calcium or to iodine.

Figure 14:
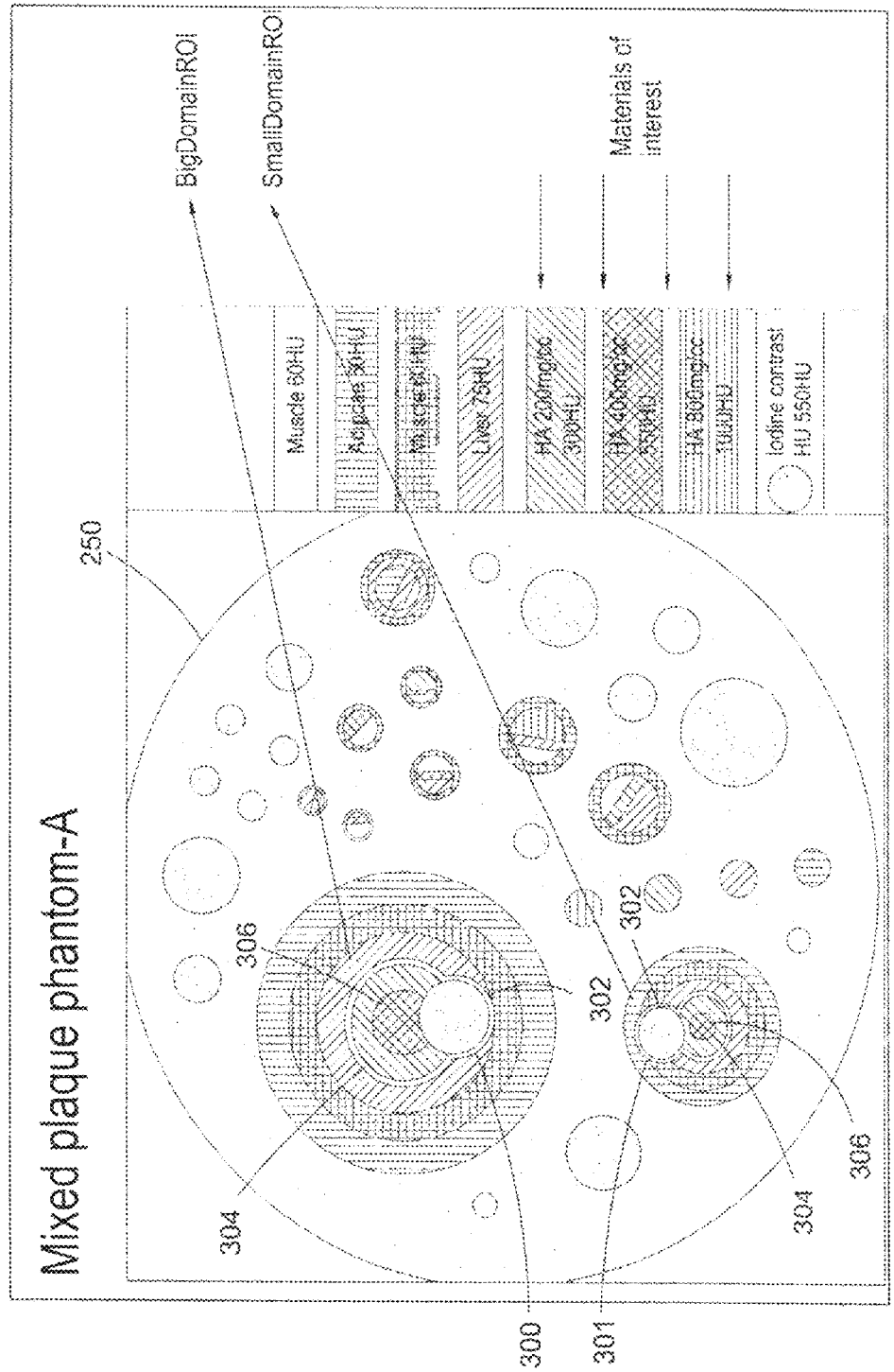
FIG. 14 is an illustration of a mixed plaque phantom.

The embodiment described above with reference to FIGS. 3 and 13 was prototyped and tested on dual-energy image data from a mixed plaque phantom 250. A phantom may be a structure that has known properties under imaging, for example known properties under CT imaging. The mixed plaque phantom 250 is illustrated in FIG. 14. The mixed plaque phantom 250 contains structures with different types of calcium (marked as HA200, HA400 and HA800) bordering iodine. The mixed plaque phantom 250 of FIG. 14 was imaged with a low energy CT scan at a peak energy of 80 kV and a high energy CT scan at a peak energy of 135 kV.

The embodiment of FIGS. 3 and 13 was tested on images of two regions of interest 300, 301 in the mixed plaque phantom. Each of the regions of interest 300, 301 comprises a region of iodine 302, a first calcium region 304, and a second calcium region 306.

In FIG. 14, the first calcium region 304 has a density of 200 mg/cc, and is expected to have a CT value of 300 HU in a high energy scan. The second calcium region 306 has a density of 400 mg/cc, and is expected to have a CT value of 550 HU in a high energy scan. The iodine region 302 is of a single concentration, and is expected to have a CT value of 550 HU.

The calcium densities and iodine concentrations used in the tests detailed below differed in some aspects from the concentrations shown in FIG. 15. Tests were performed with the following iodine concentrations:

| | Concentrations (water/iodine) | Ratio | HU Expected 135 kV | HU Actual 135 kV |
|---|---|---|---|---|
| Concentration 1 | 4:64 oz | 0.0625 | 400 | 450 |
| Concentration 2 | 4:(64 + 16 = 80) oz | 0.0500 | 320 | 400 |
| Concentration 3 | 4:(80 + 32 = 112) oz | 0.0350 | 257 | 360 |
| Concentration 4 | 4:(64 + 32 + 32 = 128) oz | 0.0312 | | 270 |

In a first test, the iodine region 302 of the larger region of interest 300 of the mixed plaque phantom 250 was filled with iodine at a high concentration (Concentration 1). The first calcium region 304 was filled with calcium having a first density and the second calcium region 306 was filled with calcium having a second density. The density of calcium regions 304 and 306 was kept the same throughout the tests described with reference to FIGS. 15 to 18.

A three-dimensional sub-volume was defined on the dual-energy image data which comprised the large region of interest 300. The three-dimensional sub-volume contains the large region of interest in x, y and z. The three-dimensional sub-volume extends over the full extent of the phantom 250 in the z direction (the direction perpendicular to the face shown in FIG. 14).

Figure 15A:
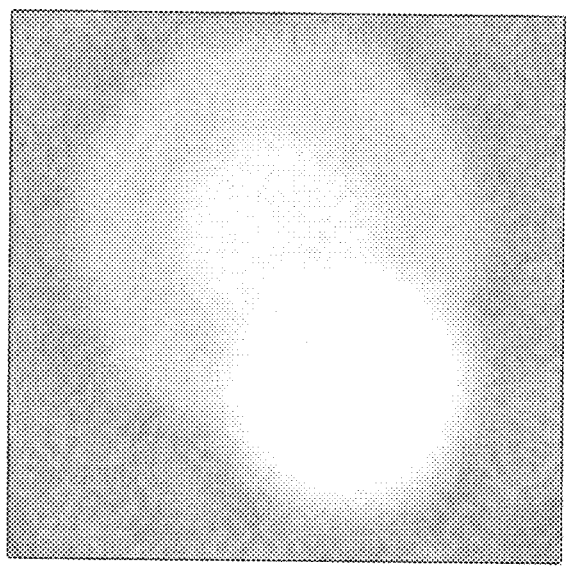
FIGS. 15a to 15h represent the experimental results from a large region of interest having a high iodine concentration.
Figure 15B:
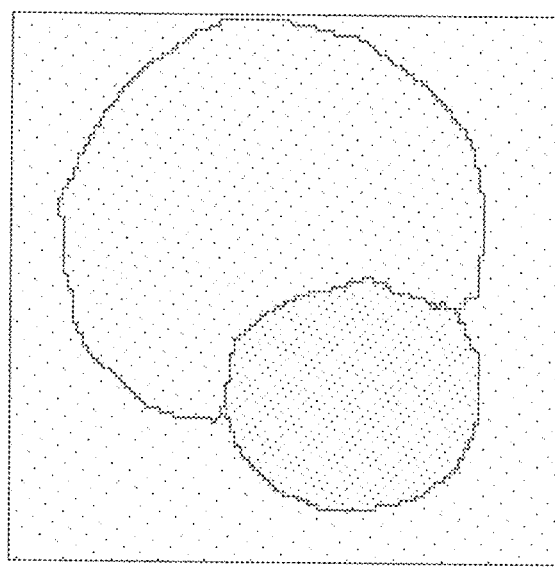

FIG. 15a shows a CT image of the larger region of interest 300. Since the image is of a known phantom, it is known in advance which voxels represent iodine and which voxels represent calcium, which can be called the expected region labeling. (Information about which voxels represent iodine and which voxels represent calcium is not provided to the algorithm of FIGS. 3 and 13.) FIG. 15b shows a version of the image of the larger region of interest in which voxels known to represent calcium have been colored in dark grey, and voxels known to represent iodine have been colored in light grey.

Figure 15C:
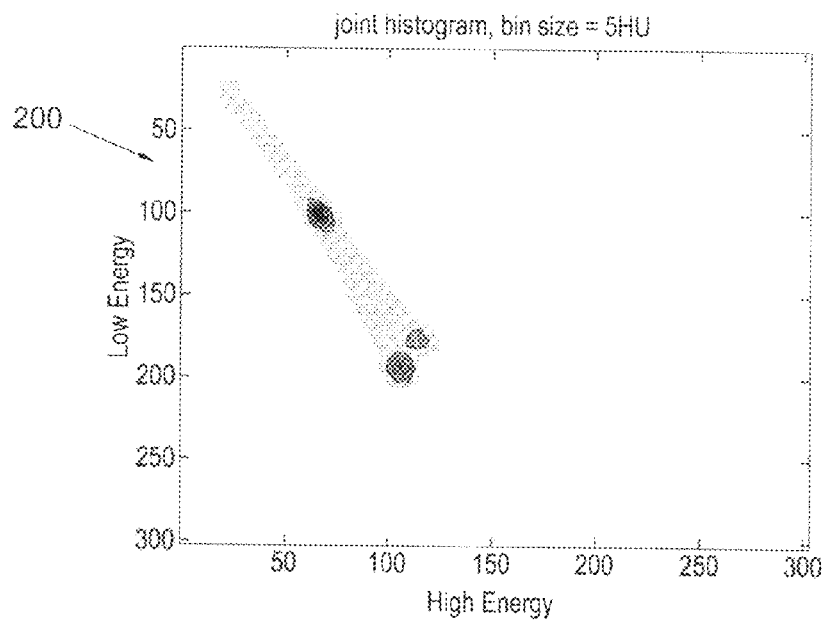

FIG. 15c is a joint histogram 200 of the voxels from the image of FIG. 15a. A filter has been applied to filter out voxels which may be neither calcium nor iodine. Three clusters of voxels are present in FIG. 15c.

Figure 15D:
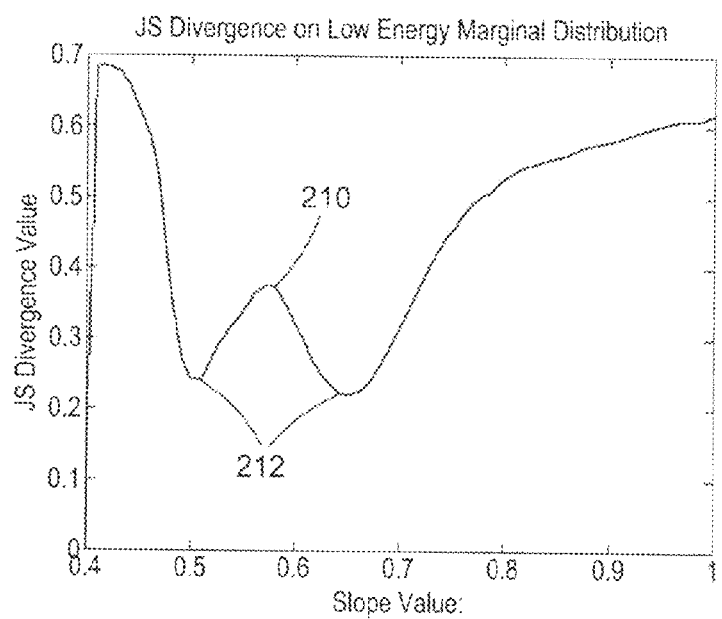
Figure 15E:
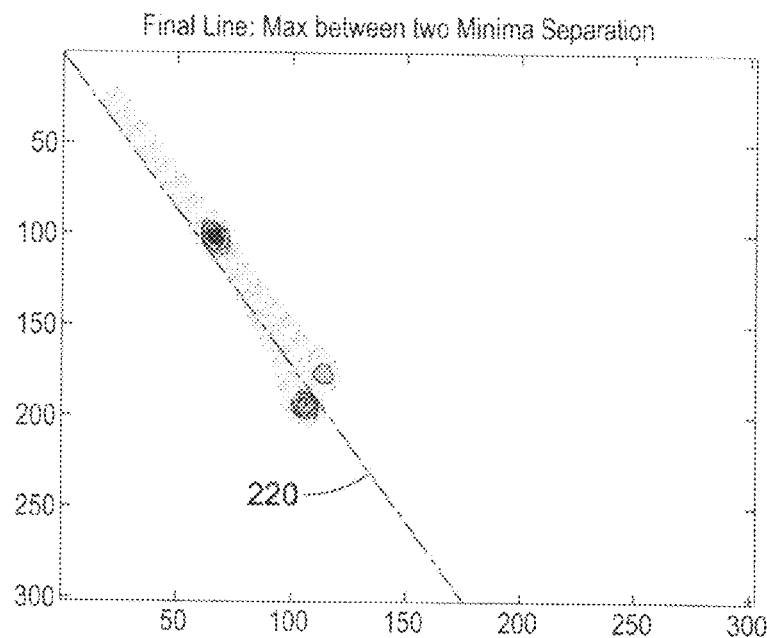

FIG. 15d is a plot of Jensen-Shannon divergence versus slope for a set of candidate thresholds 208 defined on the joint histogram 200 of FIG. 15c. The plot has a maximum 210 between two minima 212, indicating that two materials (two dissimilar distributions) may be represented in the joint histogram 200. FIG. 15e shows the joint histogram 200 partitioned by the selected threshold 220 for which the slope corresponds to the local maximum of the plot in FIG. 15d.

Figure 15F:
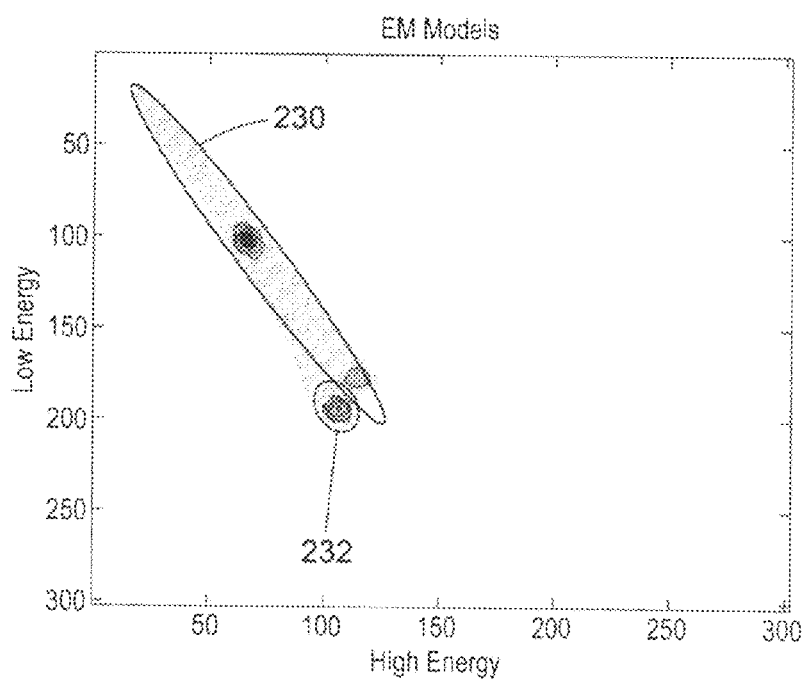
Figure 15G:
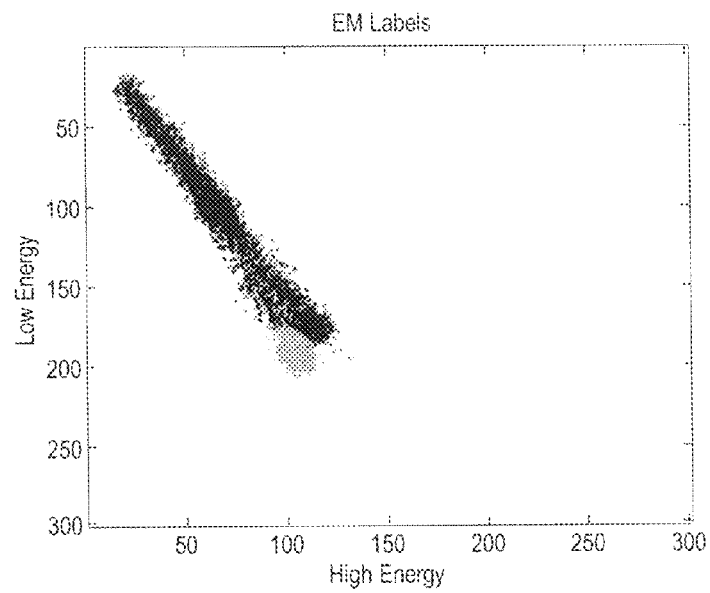
Figure 15H:
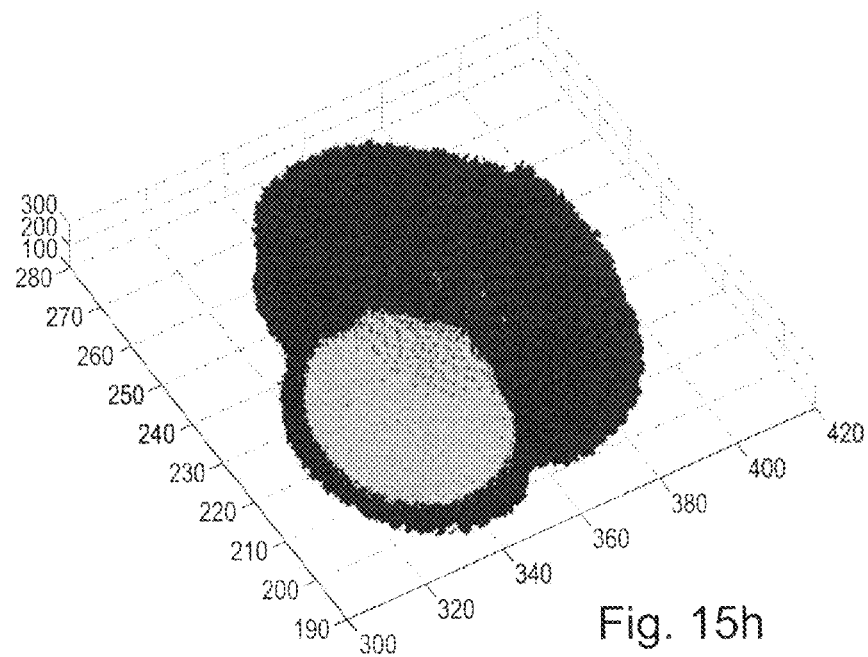

FIG. 15f shows ellipses 230 and 232 that were determined by the classification unit 28 at stage 58 of the process of FIG. 3. FIG. 15g shows the resulting labeling of voxels as calcium (dark grey) and iodine (light grey). FIG. 15h shows a three-dimensional plot of the labeled voxels.

In a second test, the iodine region 302 of the smaller region of interest 301 of the mixed plaque phantom 250 was filled with iodine at a high concentration (Concentration 1). A three-dimensional sub-volume was defined on the dual-energy image data. The sub-volume comprises all of the small region of interest 301, over the full z extent of the phantom.

Figure 16A:
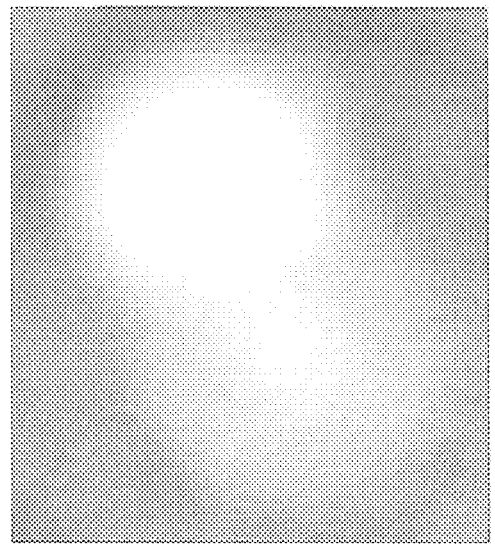
FIGS. 16a to 16h represent the experimental results from a small region of interest having a high iodine concentration.
Figure 16B:
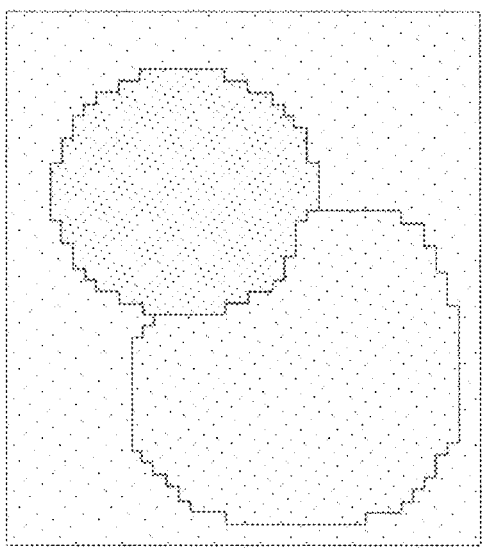

FIG. 16a shows a CT image of the smaller region of interest 301. FIG. 16b shows a version of the image of the smaller region of interest in which voxels known to represent calcium have been colored in dark grey, and voxels known to represent iodine have been colored in light grey.

Figure 16C:
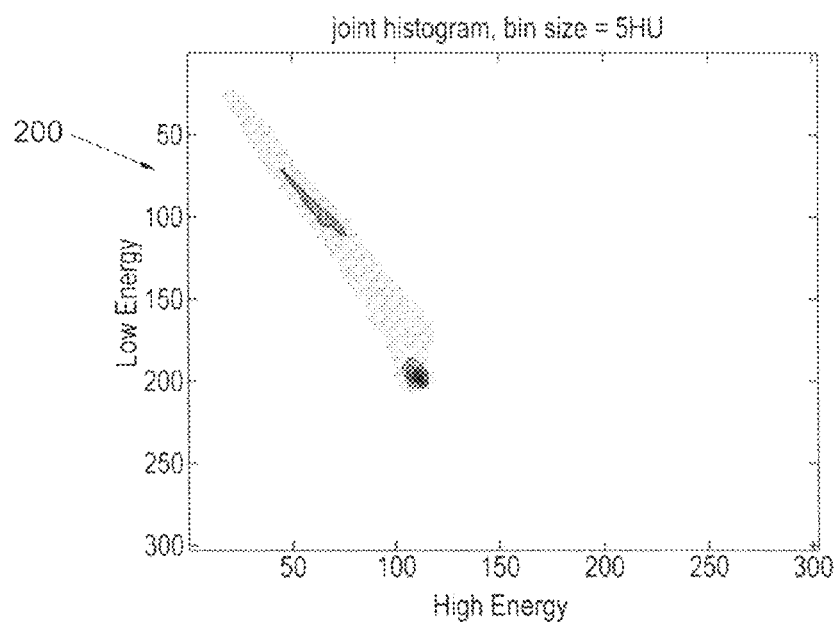

FIG. 16c is a joint histogram 200 of the voxels from the image of FIG. 16a. A filter has been applied to filter out voxels which may be neither calcium nor iodine. One small, distinct cluster of voxels and a more extended cluster of voxels are present in FIG. 16c.

Figure 16D:
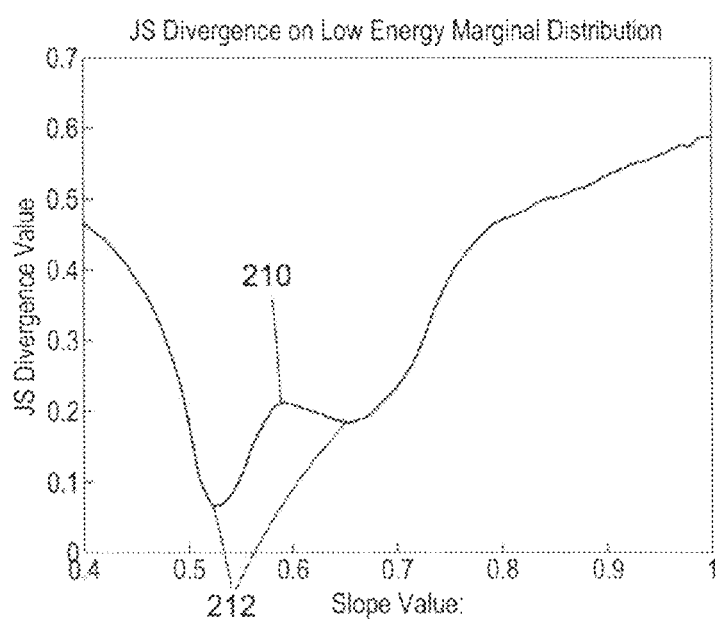
Figure 16E:
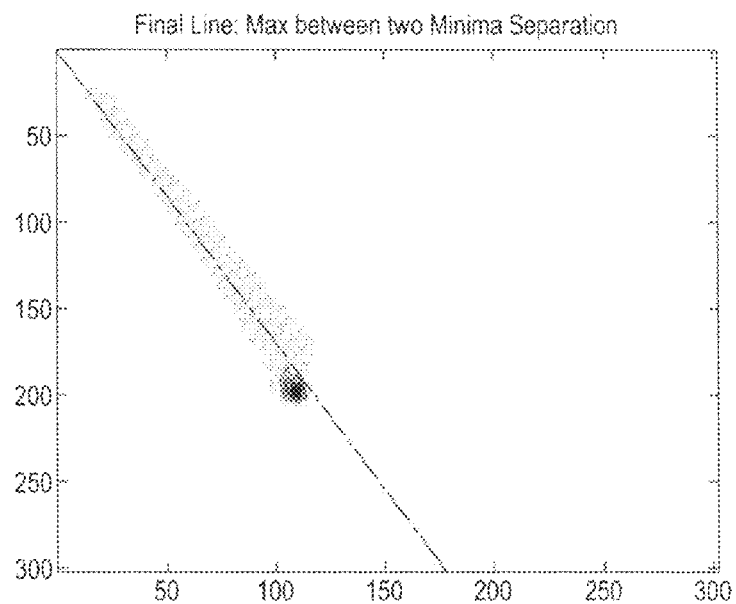

FIG. 16d is a plot of Jensen-Shannon divergence versus slope for a set of candidate thresholds 208 defined on the joint histogram 200 of FIG. 16c. The plot has a maximum 210 between two minima 212. FIG. 16e shows the joint histogram 200 partitioned by the selected threshold 220 for which the slope corresponds to the local maximum of the plot in FIG. 16d.

Figure 16F:
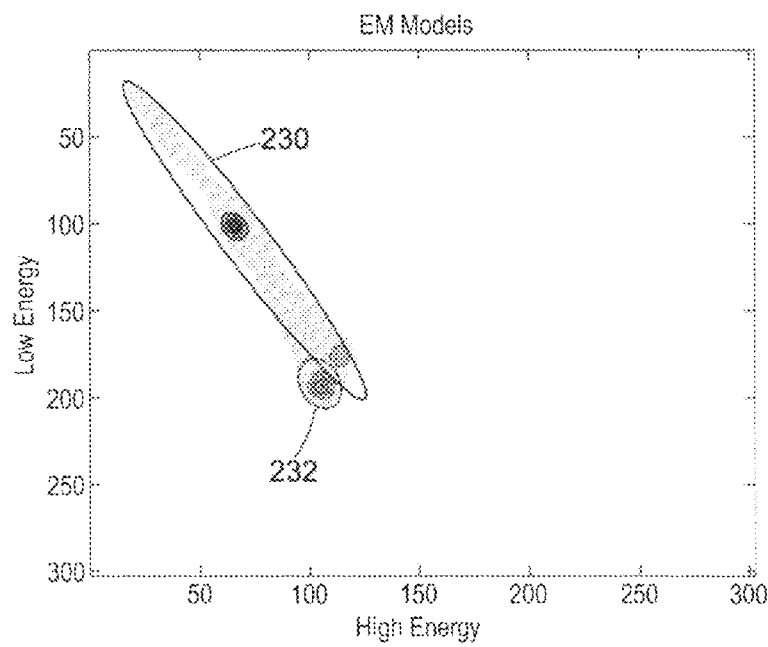
Figure 16G:
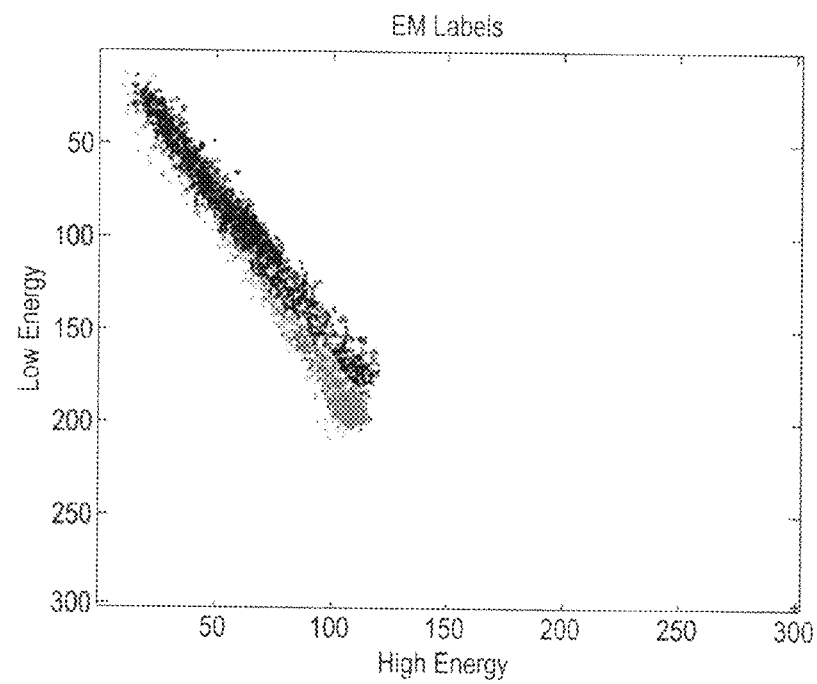
Figure 16H:
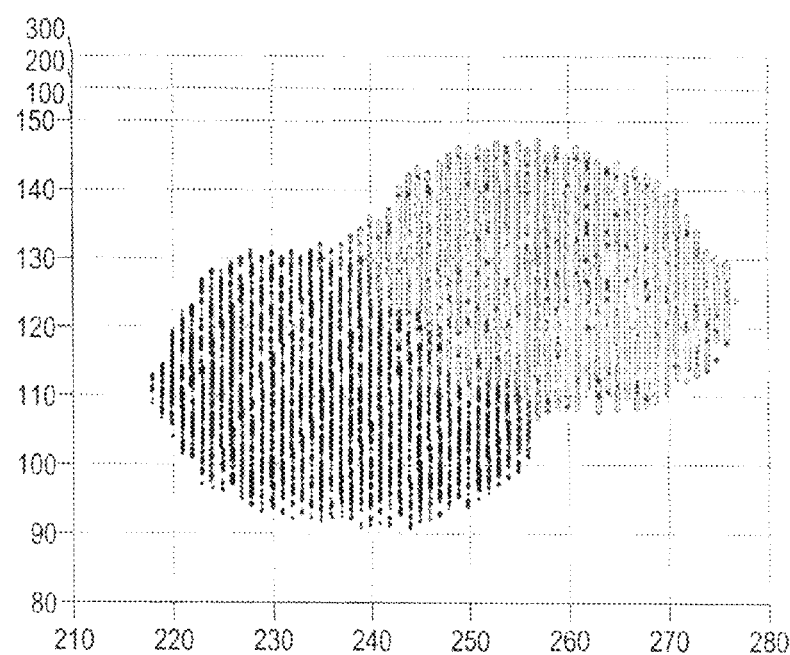

FIG. 16f shows ellipses 230 and 232 that were determined by the classification unit 28 at stage 58 of the process of FIG. 3. FIG. 16g shows the resulting labeling of voxels as calcium (dark grey) and iodine (light grey). FIG. 16h shows a three-dimensional plot of the labeled voxels. (Note that the orientation of FIG. 16h differs from the orientation of FIG. 16a and FIG. 16b).

In a third test, the iodine region 302 of the large region of interest 300 of the mixed plaque phantom 250 was filled with iodine at a low concentration (Concentration 4). A three-dimensional sub-volume was defined on the dual-energy image data. The sub-volume comprises all of the large region of interest 300, over the full z extent of the phantom.

Figure 17A:
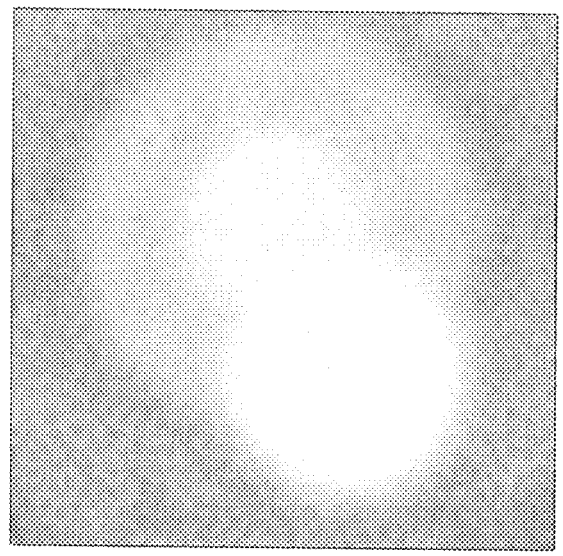
FIGS. 17a to 17h represent the experimental results from a large region of interest having a low iodine concentration.
Figure 17B:
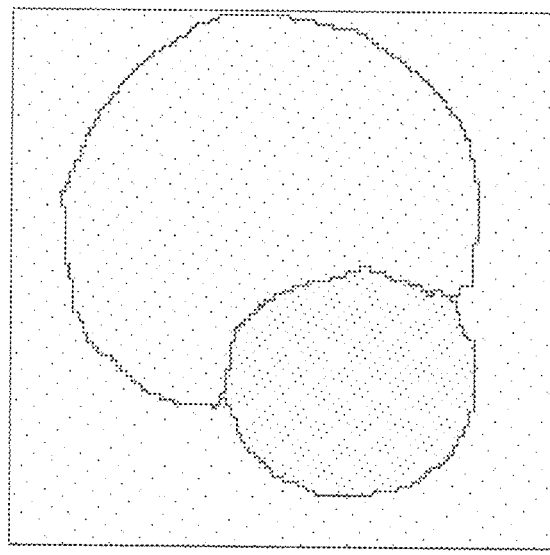

FIG. 17a shows a CT image of the large region of interest 300. FIG. 17b shows a version of the image of the large region of interest 300 in which voxels known to represent calcium have been colored in dark grey, and voxels known to represent iodine have been colored in light grey.

Figure 17C:
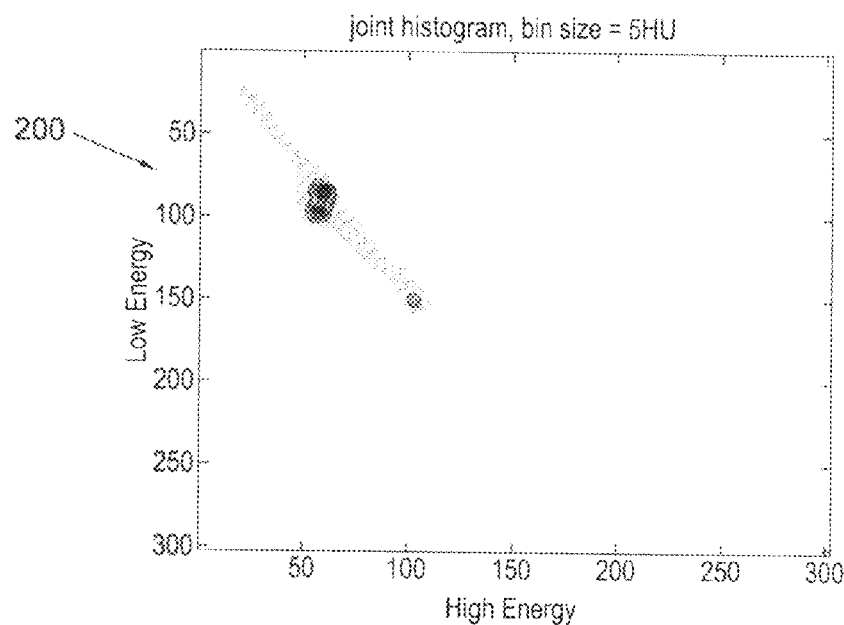

FIG. 17c is a joint histogram 200 of the voxels from the image of FIG. 17a. A filter has been applied to filter out voxels which may be neither calcium nor iodine. Two overlapping clusters are present in FIG. 17c.

Figure 17D:
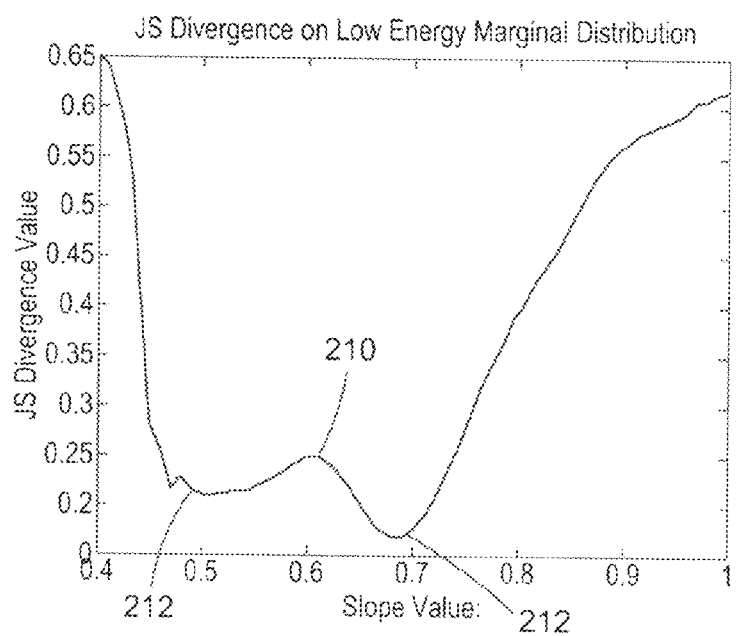
Figure 17E:
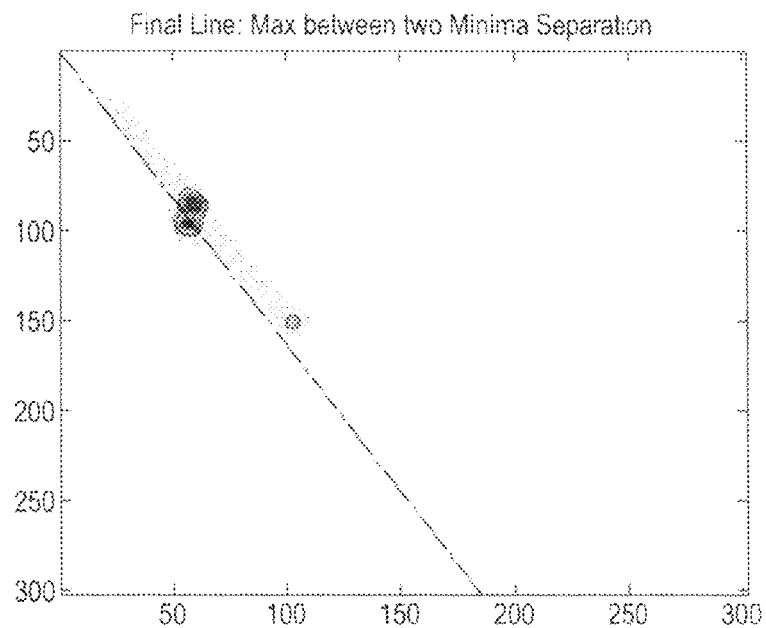

FIG. 17d is a plot of Jensen-Shannon divergence versus slope for a set of candidate thresholds 208 defined on the joint histogram 200 of FIG. 17c. The plot has a maximum 210 between two minima 212. FIG. 17e shows the joint histogram 200 partitioned by the selected threshold 220 for which the slope corresponds to the local maximum of the plot in FIG. 17d.

Figure 17F:
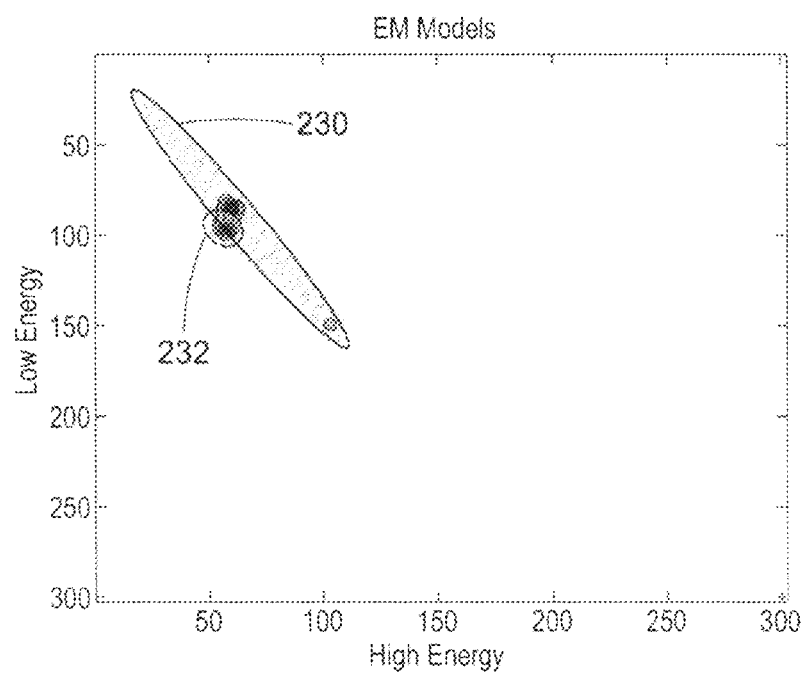
Figure 17G:
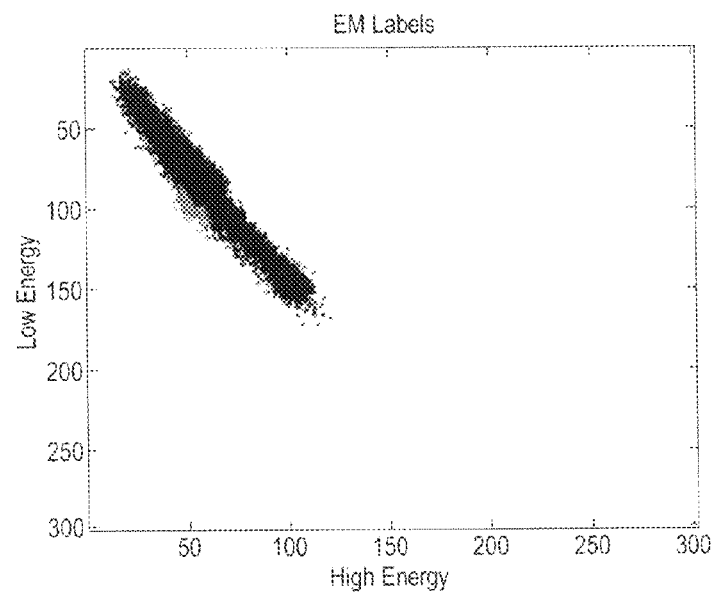
Figure 17H:
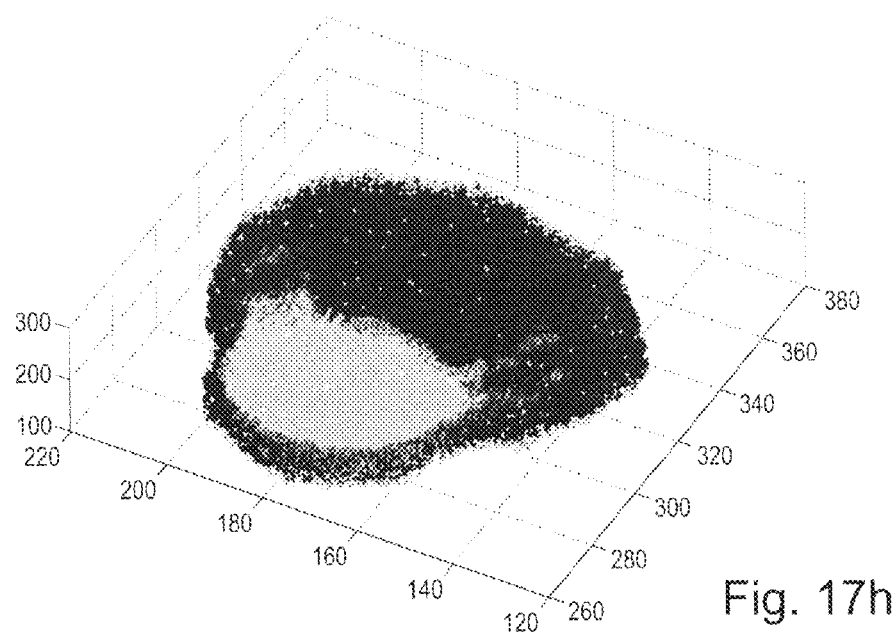

FIG. 17f shows ellipses 230 and 232 that were determined by the classification unit 28 at stage 58 of the process of FIG. 3. FIG. 17g shows the resulting labeling of voxels as calcium (dark grey) and iodine (light grey). FIG. 17h shows a three-dimensional plot of the labeled voxels. (The orientation of FIG. 17h differs from the orientation of FIG. 17a and FIG. 17b).

In a fourth test, the iodine region 302 of the smaller region of interest 301 of the mixed plaque phantom 250 was filled with iodine at a low concentration (Concentration 4). A three-dimensional sub-volume was defined on the dual-energy image data. The sub-volume comprises all of the small region of interest 301, over the full z extent of the phantom.

Figure 18A:
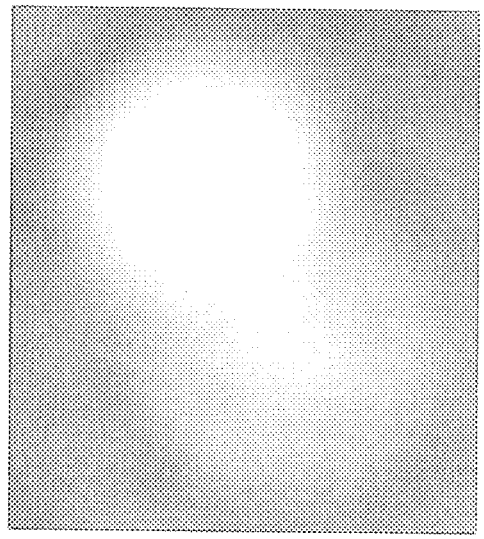
FIGS. 18a to 18h represent the experimental results from a small region of interest having a low iodine concentration.
Figure 18B:
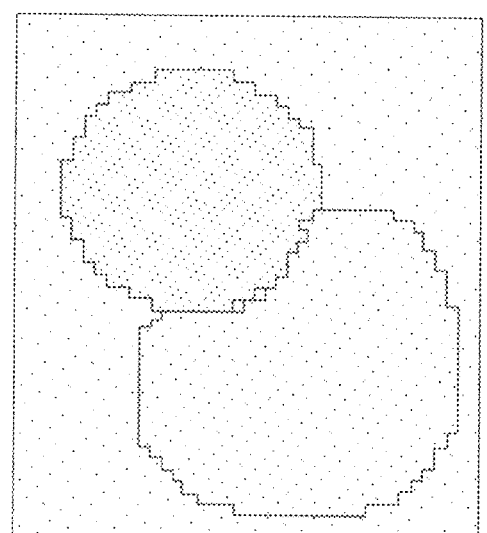

FIG. 18a shows a CT image of the smaller region of interest 301. FIG. 18b shows a version of the image of the smaller region of interest in which voxels known to represent calcium have been colored in dark grey, and voxels known to represent iodine have been colored in light grey.

Figure 18C:
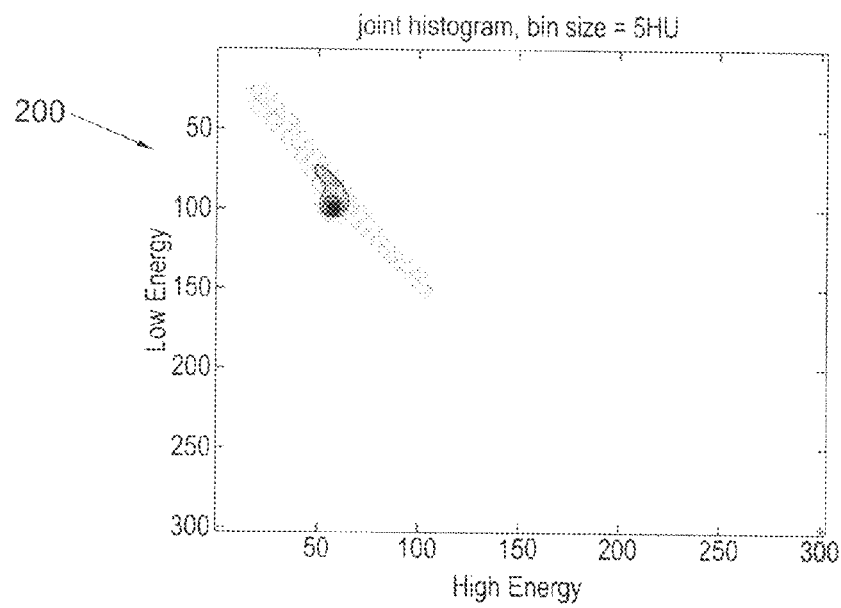

FIG. 18c is a joint histogram 200 of the voxels from the image of FIG. 18a. A filter has been applied to filter out voxels which may be neither calcium nor iodine. One distinct cluster of voxels and a more extended region of voxels are present, and overlapping, in FIG. 18c.

Figure 18D:
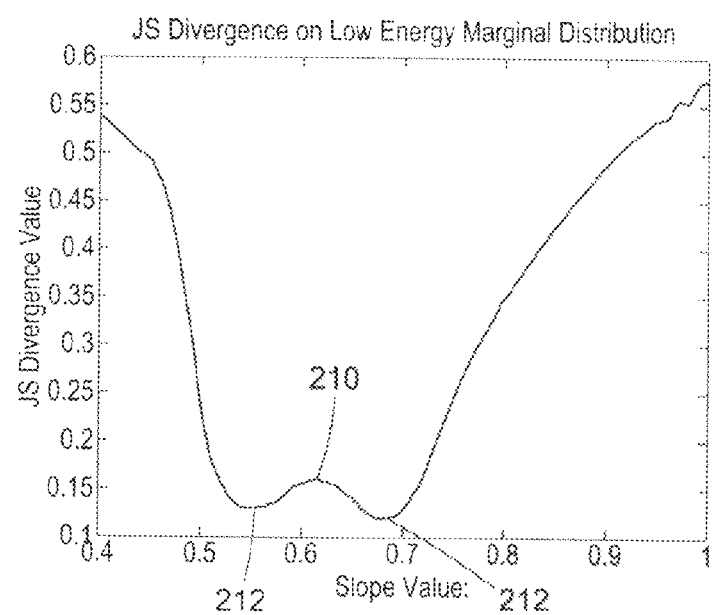
Figure 18E:
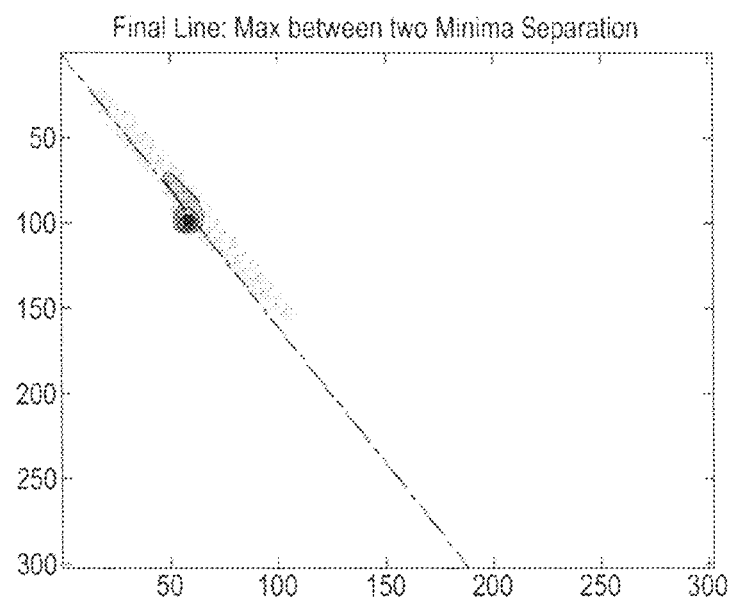

FIG. 18d is a plot of Jensen-Shannon divergence versus slope for a set of candidate thresholds 208 defined on the joint histogram 200 of FIG. 18c. The plot has a maximum 210 between two minima 212. FIG. 18e shows the joint histogram 200 partitioned by the selected threshold 220 for which the slope corresponds to the local maximum of the plot in FIG. 18d.

Figure 18F:
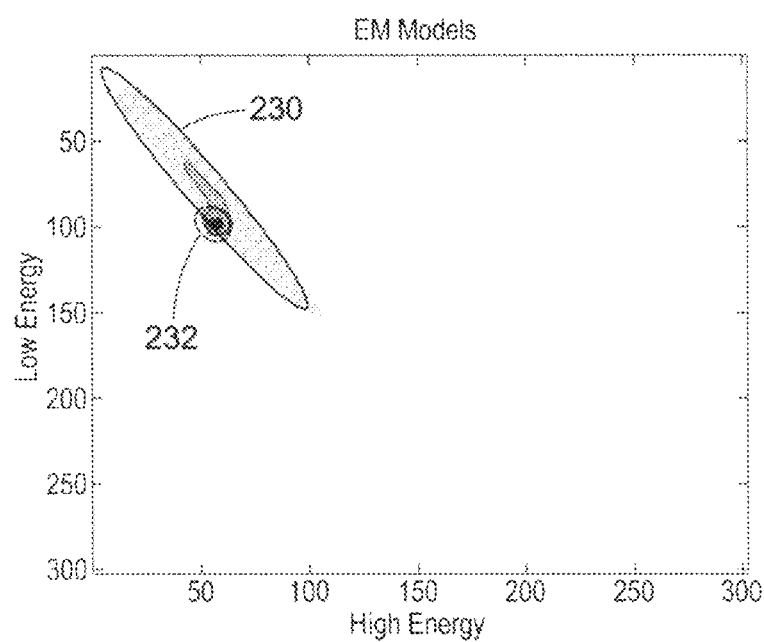
Figure 18G:
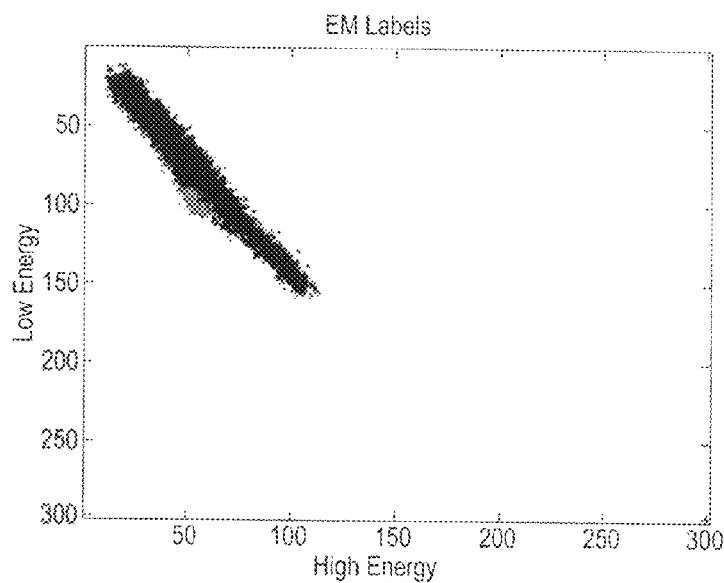
Figure 18H:
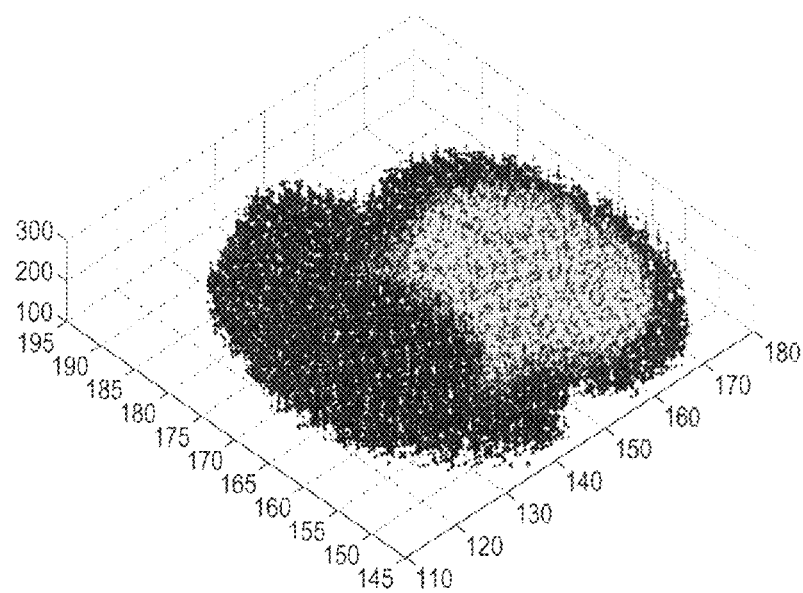

FIG. 18f shows ellipses 230 and 232 that were determined by the classification unit 28 at stage 58 of the process of FIG. 3. FIG. 18g shows the resulting labeling of voxels as calcium (dark grey) and iodine (light grey). FIG. 18h shows a three-dimensional plot of the labeled voxels. (The orientation of FIG. 18h differs from the orientation of FIG. 18a and FIG. 18b).

The results of FIGS. 15a to 18h demonstrate separation of materials at high and low iodine concentrations. A system which can isolate iodine in even low concentrations may provide physicians with a choice to use a lower iodine concentration than may otherwise be used. The process of FIG. 3 may perform robustly in scenarios with varying iodine concentrations.

In the embodiment of FIG. 3, a user selects an image region and the region selection unit 24 determines a three-dimensional sub-volume of the image volume in dependence on the user's selection.

In alternative embodiments, the region selection unit 24 may determine a two- or three-dimensional sub-volume of the image volume automatically or semi-automatically using any appropriate method.

In one embodiment, the region selection unit 24 selects at least one sub-volume of the image volume that includes voxels that have a high intensity compared to the average voxel intensity. Any suitable region selection method based on intensity may be used.

In some embodiments, the region selection unit 24 determines at least one sub-volume in dependence on a segmentation of the image data.

In some embodiments, the region selection unit 24 determines a plurality of possible image regions and displays each of the possible image regions on the image that is displayed to the user. For example, in one embodiment, the region selection unit 24 displays a set of squares on a rendered two-dimensional image (for example an axial slice), each square representing the boundary of a possible image region. The user selects one of the possible image regions, for example by clicking in one square. The region selection unit 24 determines a three-dimensional sub-volume of the image volume in dependence on which square is clicked by the user.

In one embodiment, the region selection unit 24 divides the image data volume into a plurality of three-dimensional sub-volumes, for example by determining a grid in the coordinate space of the image data set 100 and dividing the image volume into sub-volumes in accordance with the grid. The region selection unit 24 then selects a first sub-volume on which to perform the remaining steps of the process of FIG. 3. In one such embodiment, the process of FIG. 3 is repeated for each of the determined regions.

Although the description of the process of FIG. 3 is based on a single sub-volume, in some embodiments the process of FIG. 3 may be repeated for any number of sub-volumes up to and including a number of sub-volumes that covers the entire image volume.

In some embodiments, it has been found that the separation process of FIG. 3 may work better when performed on a relatively small sub-volume than when performed on a larger sub-volume, or when performed on the entire image volume. Therefore, when the process of FIG. 3 is to be used on a large volume such as the entire image volume, the region selection unit 24 may divide the large volume into smaller sub-volumes.

For example, in some embodiments a maximum sub-volume size is defined in the region selection unit 24. If the user selects a sub-volume that is greater in size than the defined maximum sub-volume size, the region selection unit 24 divides the selected sub-volume into smaller sub-volumes, which are smaller than the maximum sub-volume size.

Although in principle there are no upper limits or lower limits on the size of the sub-volume, in some embodiments the size of the sub-volume has an effect on the separation power of the method of FIG. 3. For a very small sub-volume, the method may not work well because of a low sample count. However, for a very large sub-volume (for example the whole volume), the discrimination or separation power of the method may be reduced. Materials which are not well represented in the chosen sub-volume may not be well separated.

In the embodiment of FIG. 3, a marginal distribution is obtained for region A which comprises the ILow values of the voxels having intensities in region A (for example by projecting region A of the joint histogram 200 onto the ILow axis), and a marginal distribution is similarly obtained for region B, also comprising ILow values.

In alternative embodiments, a marginal distribution may be obtained for each region which comprises the High values of the voxels having intensities in that region, for example by projecting the region onto the IHigh axis). However, it has been found that in some circumstances, calculating a Jensen-Shannon divergence of marginal distributions of ILow values may produce better separation or more robust results than calculating a Jensen-Shannon divergence of marginal distributions of IHigh values.

In the embodiment of FIG. 3, an iterative process is performed on a set of candidate thresholds 208 and the best candidate threshold 220 is selected to separate a region in which voxels are initially labeled as calcium from a region in which voxels are initially labeled as iodine.

In alternative embodiments, a threshold is selected using an optimization process, for example by determining a first candidate threshold 208 and then optimizing that candidate threshold 208 based on a cost function. Either iterating the threshold or optimizing the threshold may be described as adaptively changing the threshold. Any suitable means of adaptively changing the threshold may be used.

In one embodiment, a Jensen-Shannon divergence is calculated for a first candidate threshold 208. The candidate threshold 208 is optimized by changing the threshold until a local maximum in the Jensen-Shannon divergence curve is reached. The threshold determination unit 26 selects a threshold with values for the slope and intercept corresponding to the local maximum in the Jensen-Shannon divergence.

In some embodiments, a different quantity, for example another metric that is not the Jensen-Shannon divergence, may be used to determine a statistical dissimilarity between the distribution above the threshold and the distribution below the threshold.

Although the process of FIG. 3 describes an initial labeling based on Jensen-Shannon divergence and a further, refined labeling from an EM algorithm, in further embodiments only the stages of FIG. 3 up to the initial labeling at stage 54 are performed. The initial labels determined at stage 54 may be provided to another process, for example as inputs to a further labeling process that does not comprise expectation maximization.

Although the process of FIG. 3 comprises expectation maximization, in other embodiments any suitable model estimation algorithm may be used.

The process of FIG. 3 is described above with reference to a joint histogram having three clusters of voxels. In practice, any number of clusters may be present in the joint histogram. The aim of the clustering algorithm of the process of FIG. 3 (which may comprise expectation maximization) is to group the initial number of clusters in the joint histogram (for example, three, four, five or more) into two final clusters, one of iodine and one of calcium, as represented for example by the ellipses of FIG. 10.

The process of FIG. 3 is described for the separation of calcium voxels and iodine voxels. However, the process of FIG. 3 may be applied to any pair of materials which may be distinguishable in intensity by the method of FIG. 3. Such embodiments may use a different filter, or no filter, at stage 44. Embodiments for separation of a pair of materials that are not calcium and iodine may use different slope values or intercepts than may be used for calcium and iodine. The process of FIG. 3 may be used in particular when the intensities of the materials to be separated are such it is not possible to use a fixed threshold to separate the materials.

If separation of two materials is required, it may be possible to find a pair of CT scan energies (a low scan energy and a high scan energy) that may provide adequate separation of the material in terms of mass attenuation constant. The method of FIG. 3 may then be used to automatically separate the materials. The method of FIG. 3 is not restricted to use with calcium and iodine, but may be applied generally to other materials.

Furthermore, although the method of FIG. 3 is described in relation to the separation of two materials, in further embodiments the method of FIG. 3 may be extended to use with more than two scan energies. For example, in the case of a multispectral acquisition at N energies, the method may be extended, having a joint histogram of N dimensions rather than of two dimensions.

In an embodiment having an N-dimensional histogram, each marginal histogram will have N−1 dimensions. Instead of materials being separated with a line (threshold 220), the separating threshold may be a hyper surface.

In some embodiments, the process of FIG. 3 may be used as part of a labeling process which also includes other methods of obtaining voxel labels.

In one such embodiment, a labeling system comprises the region selection unit 24, threshold determination unit 26 and classification unit 28 of FIG. 2, but also comprises further units configured to perform alternative clustering and/or labeling methods. In one embodiment, the system comprises a computing apparatus 12 similar to that represented in FIG. 2, and the region selection unit 24, threshold determination unit 26 and classification unit 28 are implemented in computing apparatus 12 by means of a computer program having computer-readable instructions that are executable to perform the method of the embodiment.

In other embodiments, any suitable hardware may be used, which may be different from the hardware of FIG. 2.

Figure 19:
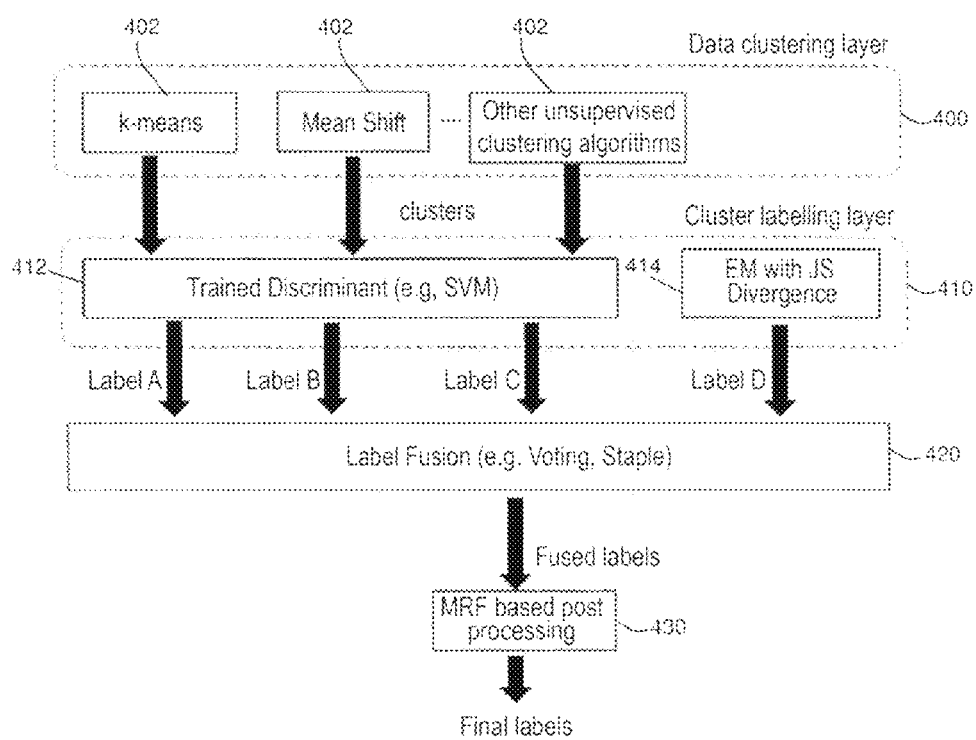
FIG. 19 is a flowchart illustrating in overview an implementation of an embodiment in a labeling process.

A schematic diagram of units implemented in a labeling system is shown in FIG. 19.

A data clustering layer 400 comprises clustering units 402. Each clustering unit performs a method of clustering on the data of image data subset 110. Some clustering methods may be based purely on intensity, while others may be based on both intensity and spatial information. Methods of clustering may include, for example, k-means, mean shift and other unsupervised clustering algorithms. Each clustering unit 402 may output raw cluster regions.

Each clustering unit 402 in data clustering layer 400 provides input to at least one clustering labeling unit 412 in a cluster labeling layer 410. A cluster labeling unit 412 may comprise a trained discriminant, for example SVM. Each raw cluster region may be labeled with a confidence level as either calcium or iodine, for example by using a trained discriminant.

In the embodiment of FIG. 19, a labeling unit 414 comprises the region selection unit 24, threshold determination unit 26 and classification unit 28 of FIG. 2. The labeling unit 414 performs expectation maximization initialized using labels derived from Jensen-Shannon divergence, as described in the flowchart of FIG. 3. The labeling unit 4141 thereby performs both clustering and labeling, and so may be considered in some systems to be part of both the data clustering layer 400 and the cluster labeling layer 410.

Each cluster labeling unit 412 and labeling unit 414 passes a set of labels for the voxels in the subset 110 to a label fusion unit 420 (which may also be described as a label fusion layer). The label fusion unit 420 fuses the labels received from each cluster labeling unit 412. For each voxel, the label fusion unit 420 receives multiple labels from the cluster labeling units 412 and labeling unit 414. For example, the label fusion unit 420 may be receive, for each voxel, one label from each cluster labeling unit 412 and one label from the labeling unit 414. In some embodiments, at least one of the labels is a binary label. In some embodiments, at least one of the labels is a probabilistic label. The label fusion unit 420 then resolves any conflicts between the labels and outputs one label for the voxel. In some embodiments, the resulting label is binary. In some embodiments, the resulting label is probabilistic. The label fusion unit 420 may use any appropriate label fusion method, for example voting or STAPLE (Simultaneous Truth and Performance Level Estimation).

The label fusion unit 420 outputs a consolidated set of labels, one label for each voxel In the present embodiment, label fusion unit 420 passes the consolidated set of labels to a post-processing unit 430 which performs MRF (Markov Random Field) based post-processing on the fused labels to obtain a set of final labels for the voxels in the subset. The post-processing may be described as cleaning up the labels using local properties.

In other embodiments, the MRF post-processing stage may be omitted or an alternative post-processing stage may be performed.

In some embodiments, by using several different clustering methods and/or different labeling methods, greater accuracy of labeling may be achieved than is achieved using any one of the clustering and/or labeling methods.

The system of FIG. 9 may extract and label calcium and iodine from an image data set 100 in a semi-supervised fashion.

Certain embodiments provide an apparatus for processing multi-energy image data to separate at least two types of material, the apparatus comprising a classification unit, wherein the classification unit is configured to obtain a classification of voxels belonging to the types of material based on a threshold which is determined in dependence on multi-energy intensity information associated with the voxels.

Certain embodiments provide an apparatus for processing volumetric image data to separate and identify iodine and calcium regions, comprising a region identification unit for identification of a local region of interest with a user interface; a label generation unit for generating rough labels for calcium, the label generation process comprising separating voxels belonging to calcium from voxels belonging to iodine using a probability distribution distance metric as a cost function for finding a model that best separates iodine voxels from calcium voxels; and a model estimation unit configured to perform a model generation process initialized with the rough labels.

In some embodiments, the local region of interest is defined automatically. In some embodiments, the probability distribution distance metric calculates a mutual statistical dependence between two distributions to be compared. Different quantities that may be used individually or in combination to form a metric may comprise Jensen-Shannon divergence, mutual information, or entropy (marginal or joint).

In some embodiments, the model for separation may be linear or non-linear. In some embodiments, the process to find the optimal separation model is an iterative method or is formulated as an optimization problem.

In some embodiments, the model estimation unit generates a Gaussian mixture model using an Expectation Maximization algorithm. In some embodiments, the model estimation unit generates models other than a Gaussian mixture.

Some embodiments incorporate as a subsystem an apparatus for processing volumetric image data to separate and identify iodine and calcium regions, comprising a region identification unit for identification of a local region of interest with a user interface; a label generation unit for generating rough labels for calcium, the label generation process comprising separating voxels belonging to calcium from voxels belonging to iodine using a probability distribution distance metric as a cost function for finding a model that best separates iodine voxels from calcium voxels; and a model estimation unit configured to perform a model generation process initialized with the rough labels.

Some such embodiments comprise a data clustering layer comprising a plurality of data clustering algorithms, a cluster labeling layer comprising a plurality of calcium and iodine label generating algorithms, a label fusion system and a post processing system.

In some embodiments, the data clustering algorithms cluster the data into regions each using an unsupervised clustering algorithm. In some embodiments, the calcium and iodine label generation layer generates labels using a trained discriminant. In some embodiments, the label fusion is based on majority voting or on a probabilistic approach such as Staple. In some embodiments, post processing of labels is performed to refine the classifications according to local spatial properties. In some embodiments, label post-processing is performed with an MRF labeler initialized with fused labels from the label fusion layer.

Although particular embodiments have been described above, features of any embodiment may be combined with features of any other embodiment.

It will be well understood by persons of ordinary skill of the art that embodiments may implement certain functionality by means of a computer program or computer programs having computer-readable instructions that are executable to perform the method of the embodiments. The computer program functionality could be implemented in hardware (for example by means of CPU). The embodiments may also be implemented by one or more ASICs (application specific integrated circuit) or by a mix of hardware or software.

Whilst particular units have been described herein, in alternative embodiments functionality of one or more of these units can be provided by a single unit, processing resource or other component, or functionality provided by a single unit can be provided by two or more units or other components in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An apparatus for processing multi-energy image data to separate at least two types of material, comprising:
processing circuitry configured to:
adaptively change a function of a first intensity value from a lower-energy scan and a second intensity value from a higher-energy scan, based on multi-energy intensity information associated with pixels or voxels of multi-energy image data which is taken with at least a higher-energy and a lower-energy, respectively; and
obtain a classification of pixels or voxels of multi-energy image data into pixels or voxels corresponding to each of the types of material by using the changed function as a boundary;
determine the adaptively changed function in dependence on the multi-energy intensity information associated with the pixels or voxels;
wherein the determining the adaptively changed function comprises:
determining at least one candidate threshold; and
for the or each candidate threshold,
partitioning the pixels or voxels into a first group of pixels or voxels and a second group of pixels or voxels in dependence on the candidate threshold; and
determining a statistical dissimilarity between the first group of pixels or voxels and the second group of pixels or voxels,
wherein the obtaining a classification of pixels or voxels of multi-energy image data into pixels or voxels corresponding to each of the types of material comprises:
obtaining an initial non-probabilistic classification of pixels or voxels of multi-energy image data into pixels or voxels corresponding to each of the types of material by using the adaptively changed function as the boundary; and
obtaining a further, refined probabilistic classification of pixels or voxels corresponding to each of the types of material by refining the initial classification in dependence on multi-energy intensity information associated with the pixels or voxels and spatial information associated with the pixels or voxels using a cluster filtering algorithm, and
wherein the obtaining the initial non-probabilistic classification of pixels or voxels includes an iterative method, wherein for each iteration, a line is drawn on a 2D joint histogram, then two ID marginal distributions are calculated on a low energy axis, then using the distributions to calculate a statistical dissimilarity matrix, continuing the iterations for a range of lines, and then selecting one of the lines based on detecting a signature shape.

2. An apparatus according to claim 1, wherein the obtaining an initial classification of pixels or voxels corresponding to each of the types of material comprises initially classifying pixels or voxels on one side of the adaptively changed function as a first type of material and initially classifying pixels or voxels on the other side of the adaptively changed function as a second type of material.

3. An apparatus according to claim 1, wherein the refining the initial classification in dependence on spatial information associated with the pixels or voxels comprises refining the initial classification of each pixel or voxel in dependence on the location of the pixel or voxel and intensity information associated with nearby pixels or voxels.

4. An apparatus according to claim 1, wherein the refining the initial classification comprises, as using a cluster filtering algorithm, at least one of performing a cluster model estimation algorithm, performing an iterative cluster model estimation algorithm, performing an Expectation Maximization algorithm, performing an algorithm using a Gaussian Mixture model, performing a hard partition based clustering algorithm, performing a fuzzy partition based clustering algorithm, performing a distribution based clustering algorithm, performing a density based clustering algorithm.

5. An apparatus according to claim 1, wherein the determining the adaptively changed function comprises adaptively changing the function in accordance with at least one of an optimization procedure or an iteration procedure.

6. An apparatus according to claim 5 wherein the optimization or process of iteration comprises determining at least one of a probability distribution distance metric, a Jensen-Shannon divergence, mutual information, marginal entropy, joint entropy, a metric that quantifies statistical dependence or distance between two or more probability distributions.

7. An apparatus according to claim 1, wherein the determining at least one candidate threshold comprises determining a plurality of candidate thresholds, and determining the adaptively changed threshold further comprises selecting a candidate threshold corresponding to a maximum of the statistical dissimilarity.

8. An apparatus according to claim 7, wherein the selecting a candidate threshold corresponding to a maximum of the statistical dissimilarity comprises selecting a candidate threshold corresponding to a local maximum of the statistical dissimilarity, wherein the local maximum is between two minima.

9. An apparatus according to claim 7, wherein the determining a statistical dissimilarity between the first group of pixels or voxels and the second group of pixels or voxels comprises determining a statistical dissimilarity between a distribution of intensity values associated with the first group of pixels or voxels and a distribution of intensity values associated with the second group of pixels or voxels.

10. An apparatus according to claim 9, wherein the multi-energy intensity information associated with the pixels or voxels comprises, for each pixel or voxel, at least an intensity value from a lower-energy scan and an intensity value from a higher-energy scan;
wherein the distribution of intensity values associated with the first group of pixels or voxels comprises a one-dimensional distribution of intensity values from the lower-energy scan; and
wherein the distribution of intensity values associated with the second group of pixels or voxels comprises a one-dimensional distribution of intensity values from the lower-energy scan.

11. An apparatus according to claim 10 wherein the determining the statistical dissimilarity comprises determining at least one of a probability distribution distance metric, a Jensen-Shannon divergence, mutual information, marginal entropy or joint entropy, a metric that quantifies statistical dependence or distance between two or more probability distributions.

12. An apparatus according to claim 1, wherein the multi-energy intensity information associated with the pixels or voxels comprises, for each pixel or voxel, at least a first intensity value from a lower-energy scan and a second intensity value from a higher-energy scan, and
wherein the adaptively changed threshold comprises a function of first intensity value and second intensity value.

13. An apparatus according to claim 12 wherein the function of first intensity value and second intensity value comprises a substantially straight line, and wherein determining the adaptively changed threshold comprises determining at least one of a slope and an intercept of the substantially straight line.

14. An apparatus according to claim 1, wherein the processing circuitry is further configured to receive a multi-energy image data set representative of an image volume, and to select the multi-energy image data from the multi-energy image data set, wherein the multi-energy image data is representative of a part of the image volume.

15. An apparatus for processing multi-energy image data to separate at least two types of material, comprising:
processing circuitry configured to:
adaptively change a function of a first intensity value from a lower-energy scan and a second intensity value from a higher-energy scan, based on multi-energy intensity information associated with pixels or voxels of multi-energy image data which is taken with at least a higher-energy and a lower-energy, respectively;
obtain a classification of pixels or voxels of multi-energy image data into pixels or voxels corresponding to each of the types of material by using the changed function as a boundary;
receive a multi-energy image data set representative of an image volume, and to select the multi-energy image data from the multi-energy image data set, wherein the multi-energy image data is representative of a part of the image volume,
wherein the selecting the multi-energy image data comprises at least one of a), b), c), d) and e):
a) receiving a user selection of an image region and selecting the part of the image volume in dependence on the user-selected image region;
b) automatically selecting the multi-energy image data;
c) automatically selecting the part of the image volume;
d) selecting the multi-energy image data in dependence on intensity values in the multi-energy data set;
e) dividing the image volume into a plurality of sub-volumes, wherein each sub-volume is representative of a part of the image volume, selecting one sub-volume, and selecting the multi-energy image data, wherein the multi-energy image data is representative of the selected sub-volume;
and further comprising:
determine the adaptively changed function in dependence on the multi-energy intensity information associated with the pixels or voxels;
wherein the determining the adaptively changed function comprises:
determining at least one candidate threshold; and
for the or each candidate threshold,
partitioning the pixels or voxels into a first group of pixels or voxels and a second group of pixels or voxels in dependence on the candidate threshold; and
determining a statistical dissimilarity between the first group of pixels or voxels and the second group of pixels or voxels,
wherein the obtaining a classification of pixels or voxels of multi-energy image data into pixels or voxels corresponding to each of the types of material comprises:
obtaining an initial non-probabilistic classification of pixels or voxels of multi-energy image data into pixels or voxels corresponding to each of the types of material by using the adaptively changed function as the boundary; and
obtaining a further, refined probabilistic classification of pixels or voxels corresponding to each of the types of material by refining the initial classification in dependence on multi-energy intensity information associated with the pixels or voxels and spatial information associated with the pixels or voxels using a cluster filtering algorithm, and wherein the obtaining the initial non-probabilistic classification of pixels or voxels includes an iterative method, wherein for each iteration, a line is drawn on a 2D joint histogram, then two ID marginal distributions are calculated on a low energy axis, then using the distributions to calculate a statistical dissimilarity matrix, continuing the iterations for a range of lines, and then selecting one of the lines based on detecting a signature shape.

16. An apparatus for processing multi-energy image data to separate at least two types of material, comprising:
processing circuitry configured to:
adaptively change a function of a first intensity value from a lower-energy scan and a second intensity value from a higher-energy scan, based on multi-energy intensity information associated with pixels or voxels of multi-energy image data which is taken with at least a higher-energy and a lower-energy, respectively;
obtain a classification of pixels or voxels of multi-energy image data into pixels or voxels corresponding to each of the types of material by using the changed function as a boundary;
determine the adaptively changed function in dependence on the multi-energy intensity information associated with the pixels or voxels;
wherein the determining the adaptively changed function comprises:
determining at least one candidate threshold; and
for the or each candidate threshold,
partitioning the pixels or voxels into a first group of pixels or voxels and a second group of pixels or voxels in dependence on the candidate threshold; and
determining a statistical dissimilarity between the first group of pixels or voxels and the second group of pixels or voxels
wherein the multi-energy image data comprises at least one of: dual-energy image data, CT data, volumetric image data,
wherein the obtaining a classification of pixels or voxels of multi-energy image data into pixels or voxels corresponding to each of the types of material comprises:
obtaining an initial non-probabilistic classification of pixels or voxels of multi-energy image data into pixels or voxels corresponding to each of the types of material by using the adaptively changed function as the boundary; and
obtaining a further, refined probabilistic classification of pixels or voxels corresponding to each of the types of material by refining the initial classification in dependence on multi-energy intensity information associated with the pixels or voxels and spatial information associated with the pixels or voxels using a cluster filtering algorithm, and
wherein the obtaining the initial non-probabilistic classification of pixels or voxels includes an iterative method, wherein for each iteration, a line is drawn on a 2D joint histogram, then two ID marginal distributions are calculated on a low energy axis, then using the distributions to calculate a statistical dissimilarity matrix, continuing the iterations for a range of lines, and then selecting one of the lines based on detecting a signature shape.

17. An apparatus according to claim 1, wherein the types of material comprise at least one of calcium, contrast material, iodine.

18. A system for processing multi-energy image data to separate at least two materials, the system comprising the apparatus of claim 1, wherein the processing circuitry is further configured to:
determine a plurality of data clustering regions of pixels or voxels in the multi-energy image data;
label cluster regions of pixels or voxels determined by one or more of the data clustering units;
determine a single set of labels for the pixels or voxels from the labeled cluster regions; and
refine the single set of labels.

19. A system according to claim 18, wherein at least one of a), b), c), d) and e):
a) determining cluster regions of pixels or voxels in the multi-energy image data comprises an unsupervised clustering algorithm;
b) labeling the cluster regions of pixels or voxels comprises labeling the cluster regions of pixels or voxels using a trained discriminant;
c) determining the single set of labels for the pixels or voxels comprises a label fusion process, the label fusion process comprising at least one of majority voting, probabilistic label fusion or Simultaneous Truth and Performance Level Estimation;
d) refining the single set of labels comprises refining the single set of labels in dependence on spatial information associated with the pixels or voxels;
e) refining the single set of labels comprises refining the single set of labels using an Markov Random Field labeler.

20. A method for processing multi-energy image data to separate at least two types of material, comprising:
adaptively changing a function of a first intensity value from a lower-energy scan and a second intensity value from a higher-energy scan, based on multi-energy intensity information associated with pixels or voxels of multi-energy image data which is taken with at least a higher-energy and a lower-energy, respectively; and
obtaining a classification of pixels or voxels of multi-energy image data into pixels or voxels corresponding to each of the types of material by using the changed function as a boundary; and
determine the adaptively changed function in dependence on the multi-energy intensity information associated with the pixels or voxels;
wherein the determining the adaptively changed function comprises:
determining at least one candidate threshold; and
for the or each candidate threshold,
partitioning the pixels or voxels into a first group of pixels or voxels and a second group of pixels or voxels in dependence on the candidate threshold; and
determining a statistical dissimilarity between the first group of pixels or voxels and the second group of pixels or voxels;
wherein the obtaining a classification of pixels or voxels of multi-energy image data into pixels or voxels corresponding to each of the types of material comprises:
obtaining an initial non-probabilistic classification of pixels or voxels of multi-energy image data into pixels or voxels corresponding to each of the types of material by using the adaptively changed function as the boundary; and
obtaining a further, refined probabilistic classification of pixels or voxels corresponding to each of the types of material by refining the initial classification in dependence on multi-energy intensity information associated with the pixels or voxels and spatial information associated with the pixels or voxels using a cluster filtering algorithm, and wherein the obtaining the initial non-probabilistic classification of pixels or voxels includes an iterative method, wherein for each iteration, a line is drawn on a 2D joint histogram, then two ID marginal distributions are calculated on a low enemy axis, then using the distributions to calculate a statistical dissimilarity matrix, continuing the iterations for a range of lines, and then selecting one of the lines based on detecting a signature shape.

21. A non-transitory computer-readable storage medium storing a computer program for performing a method according to claim 20.

* * * * *